United States Patent [19]

Clark et al.

[11] Patent Number: 4,957,914
[45] Date of Patent: Sep. 18, 1990

[54] 1,9-ALKANO-BRIDGED-2,3,4,5-TETRAHYDRO-1H-3-BENZAZEPINES

[75] Inventors: Robin D. Clark, Palo Alto; Jacob Berger, Los Altos Hills; Klaus K. Weinhardt, San Francisco, all of Calif.

[73] Assignee: Syntex (U.S.A.) Inc., Palo Alto, Calif.

[21] Appl. No.: 231,818

[22] Filed: Aug. 12, 1988

Related U.S. Application Data

[62] Division of Ser. No. 50,977, May 15, 1987, abandoned.

[51] Int. Cl.$^5$ ................... C07D 223/16; C07D 223/32; C07D 223/18; A61K 31/55
[52] U.S. Cl. ..................................... 514/217; 540/581; 540/586; 564/180; 564/387
[58] Field of Search ........................ 540/581; 514/217

[56] References Cited

U.S. PATENT DOCUMENTS 4,769,368  9/1988  Kaiser ................................ 514/217

OTHER PUBLICATIONS

Hackh's Chemical Dictionary, 5th Ed. (1987), p. 30.

Primary Examiner—Mark L. Berch
Attorney, Agent, or Firm—David A. Lowin; Tom M. Moran

[57] ABSTRACT

1,9-Alkano-bridged-2,3,4,5-tetrahydro-1H-3-benzazepines and the derivatives thereof, i.e., the compounds of Formula I:

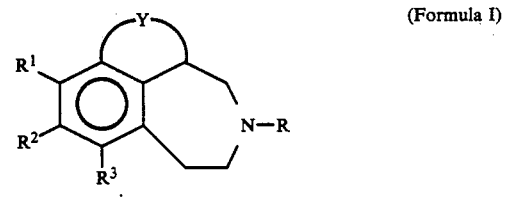

(Formula I)

wherein:
R is selected from the group consisting of: hydrogen, cyano, lower alkyl, lower alkenyl, and aralkyl;
each of $R^1$, $R^2$ and $R^3$ is independently selected from the group consisting of: hydrogen, hydroxy, halo, trifluoromethyl, nitro, amido, lower alkoxy, lower alkyl, and lower alkylthio; and
Y is lower alkylene having from two to four carbon atoms;

and the pharmaceutically acceptable salts thereof, are useful as CNS agents, e.g., as antidepressants, anxiolytics and antihypertensives, and/or as precursors thereto.

29 Claims, No Drawings

1,9-ALKANO-BRIDGED-2,3,4,5-TETRAHYDRO-1H-3-BENZAZEPINES

This is a division of pending application Ser. No. 050,977, filed May 15, 1987, incorporated herein by reference, now abandoned.

BACKGROUND OF THE INVENTION

1. Field of the Invention

The present invention relates to pharmaceutical compositions, particularly to cycloalkanoazepines and derivatives thereof, and to their use as CNS agents, e.g., as antidepressants, anxiolytics and antihypertensives. These compositions demonstrate affinity for $\alpha_2$ and $5\text{-HT}_{1A}$ receptors.

2. Background Information and Related Disclosures

Tricyclic antidepressants, such as those described in U.S. Pat. No. 3,991,059 include three six-membered rings, one of which has a nitrogen atom. Those described in French patent No. 2,493,842 include a six and a seven membered ring with a two-membered bridge, the bridge including a nitrogen atom.

U.S. Pat. No. 4,465,677 shows $\alpha_2$ antagonists for cardiovascular and antihypertensive uses, which are described as N-substituted 2,3,4,5-tetrahydro-1H-3-benzazepines, where the 6-chloro-2,3,4,5-tetrahydro-3-methyl-1H-3-benzazepine is preferred.

Compounds that are specific for $\alpha_2$ and/or $5\text{-HT}_{1A}$ and are useful as antihypertensives and cardiovascular agents have, however, remained desired.

SUMMARY OF THE INVENTION

One aspect of the present invention concerns 1,9-Alkano-bridged-2,3,4,5-tetrahydro-1H-3-benzazepines, and the derivatives thereof, i.e, the compounds of Formula I:

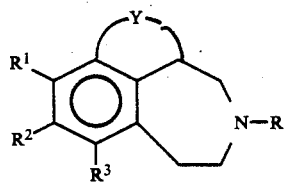

(Formula I)

wherein:
R is selected from the group consisting of: hydrogen, cyano, lower alkyl, lower alkenyl, and aralkyl;
each of $R^1$, $R^2$ and $R^3$ is independently selected from the group consisting of: hydrogen, hydroxy, halo, trifluoromethyl, nitro, amido, lower alkoxy, lower alkyl, and lower alkylthio; and
Y is lower alkylene having from two to four carbon atoms;
and the pharmaceutically acceptable salts thereof.

In yet another aspect, the invention relates to a pharmaceutical composition containing a therapeutically effective amount of a compound of Formula I or a pharmaceutically acceptable salt thereof admixed with at least one pharmaceutically acceptable excipient.

In still another aspect, the invention relates to a method of treating CNS disorders, depression, anxiety or hypertension in a mammal by administering to a mammal in need of such treatment a therapeutically effective amount of a compound of Formula I or a pharmaceutically acceptable salt thereof.

Another aspect of the invention relates to processes for making the compounds of Formula I and the pharmaceutically acceptable salts thereof, including certain precursors thereto, represented by Formula II:

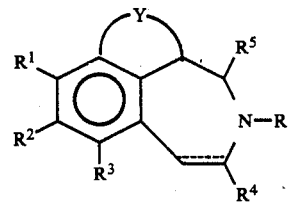

(Formula II)

wherein:
R is selected from the group consisting of hydrogen, cyano, lower alkyl, lower alkenyl, and aralkyl;
each of $R^1$, $R^2$ and $R^3$ is independently selected from the group consisting of hydrogen, hydroxy, halo, trifluoromethyl, nitro, amido, lower alkoxy, lower alkyl, and lower alkylthio;
$R^4$ is H, $H_2$ or $=O$;
$R^5$ is $H_2$ or $=O$;
Y is lower alkylene having from two to four carbon atoms; and
the dashed line represents a single or a double bond; provided that when $R^4$ is $=O$, $R^5$ is $H_2$; and
provided that when $R^5$ is $=O$, $R^4$ is H and the dashed line represents a double bond, or $R^4$ is $H_2$ and the dashed line represents a single bond.

A process for making the compounds of Formula I entails contacting a compound of Formula II with a reducing agent or an acid at conditions sufficient to convert $R^4$ or $R^5$ to $H_2$ and/or the double bond represented by the dashed line to a single bond.

DETAILED DESCRIPTION OF THE INVENTION

Definitions and General Parameters

The following definitions are set forth to illustrate and define the meaning and scope of the various terms used to describe the invention herein.

The naming and numbering of the compounds of the present invention is illustrated in Formulae III-V as follows:

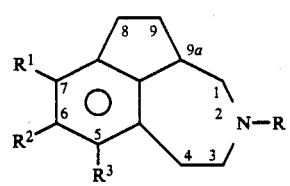

(Formula III)

The compounds of the invention in which Y is $-(CH_2)_2-$ will be named using the numbering system of Formula III, e.g., as 1,3,4,8,9,9a-hexahydro-2H-indeno[1,7-cd]azepine (where R, $R^1$, $R^2$ and $R^3$ are hydrogen).

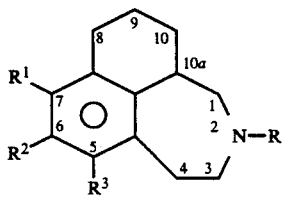

(Formula IV)

The compounds of the invention in which Y is —(CH$_2$)$_3$— will be named using the numbering system of Formula IV, e.g., as 2-methyl-1,2,3,4,8,9,10,10a-octahydronaphth[1,8-cd]azepine (where R is methyl, and R$^1$, R$^2$ and R$^3$ are hydrogen).

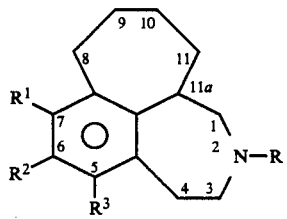

(Formula V)

The compounds of the invention in which Y is —(CH$_2$)$_4$— will be named using the numbering system of Formula V, e.g., as 1,3,4,8,9,10,11,11a,-octahydro-2H-cyclohepta[c,d][3]benzazepine (where R, R$^1$, R$^2$ and R$^3$ are hydrogen).

As used herein, the term "alkyl" refers to a fully saturated monovalent radical containing only carbon and hydrogen, and which may be a cyclic, branched or straight chain radical. This term is further exemplified by radicals such as methyl, ethyl, t-butyl, pentyl, pivalyl, heptyl and adamantyl.

The term "lower alkyl" refers to a cyclic, branched or straight chain monovalent alkyl radical of one to six carbon atoms. This term is further exemplified by such radicals as methyl, ethyl, n-propyl, isopropyl, n-butyl, t-butyl, i-butyl (or 2-methylpropyl), cyclopropylmethyl, i-amyl, n-amyl, and hexyl.

The term "alkylene" refers to a fully saturated divalent radical containing only carbon and hydrogen, and which may be a branched or straight chain radical. This term is further exemplified by radicals such as methylene, ethylene, n-propylene, t-butylene, i-pentylene, and n-heptylene.

The term "lower alkylene" refers to a divalent alkyl radical of one to six carbon atoms. This term is further exemplified by such radicals as methylene, ethylene, n-propylene, i-propylene, n-butylene, t-butylene, i-butylene (or 2-methylpropylene), isoamylene, pentylene, and n-hexylene.

The term "alkenyl" refers to a both straight-chain and branched-chain mono- or poly-olefinically-unsaturated hydrocarbyl monovalent radical containing only carbon and hydrogen, having one or more double bonds (preferably not more than two) and having no triple bonds. This term is further exemplified by radicals such as allyl; 2-methylallyl; buten-2-yl; penten-2-, 3-, or 4-yl; hexen-2-, 3-, 4-, or 5-yl; hepten-2-, 3-, 4-, 5-, or 6-yl; and pentadien-2,4-yl.

The term "aryl" refers to a substituted or unsubstituted monovalent unsaturated aromatic carbocyclic radical having a single ring (e.g., phenyl) or two condensed rings (e.g., naphthyl).

The term "aralkyl" refers to the group -R'-Ar, where Ar is an aryl group and R' is straight-chain or branched-chain lower alkylene.

As used herein, the term "halo" refers to fluoro, bromo, chloro and iodo.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

A "pharmaceutically acceptable salt" may be any salt derived from an inorganic or organic acid. The term "pharmaceutically acceptable anion" refers to the anion of such acid addition salts. The salt and/or the anion are chosen not to be biologically or otherwise undesirable.

The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluensulfonic acid and the like.

As used herein, the terms "inert organic solvent" or "inert solvent" mean a solvent inert under the conditions of the reaction being described in conjunction therewith (including, for example, benzene, toluene, acetonitrile, tetrahydrofuran, diethyl ether, chloroform, methylene chloride, pyridine and the like).

As used herein, the term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

Unless specified to the contrary, the reactions described herein take place at atmospheric pressure over a temperature range from about 10° C. to about 100° C., more preferably from about 10° C. to about 50° C., and most preferably at about room (or ambient) temperature, e.g., about 20° C.

PREPARATION OF THE COMPOUNDS OF FORMULA I

Starting Materials

For purposes of the following description of preparation of Compounds of Formula I, and in the Examples, R$^1$, R$^2$ and R$^3$ are collectively represented by the radical "X".

The compounds of Formula I are prepared, for example as illustrated in Reaction Scheme 1, from 1,2-benzo-3-oxo-cyclo-(C$_5$ to C$_7$)-alkanes, i.e., the compounds of Formula 1 where X is hydrogen (see Reaction Scheme 1), which are readily available from commercial sources. For the substituted benzene compounds of Formula I (i.e., those compounds where $R^1$, $R^2$ and/or $R^3$ are not hydrogen) the starting materials are represented by Formula 1 where X is not hydrogen; some of these materials are also commercially available, and where not, they can be easily prepared according to procedures that are well known to the art and published in the literature.

It is also possible to modify X during the course of the synthesis, for example, by halogenation or nitration of the intermediates of Formula 3 according to the procedure of Tetsuya, et al. [*Chem. Pharm. Bull.*, 25(12), 3198–3209 (1977)], or by similar reaction of Formula I-a.

The choice of a starting material depends on the desired length of Y. Thus, for example, to prepare the compounds where Y has two carbon atoms, a starting material is 1-indanone (available from Aldrich). A starting material for the compounds of Formula I where Y has three carbon atoms is 1-oxo-1,2,3,4,-tetrahydronaphthalene (or 1-tetralone, available from Aldrich). A starting material for the compounds of Formula I where Y has four carbon atoms is 1,2-benzo-3-oxo-cycloheptane (or 1-benzosuberone, available from Aldrich.)

PREPARATION OF INTERMEDIATES 2 AND 3

Referring to Reaction Scheme 1, which follows, Formula 1 can be converted to the intermediates of Formulae 2 and 3, according to the procedure described by Belletire, et al. [*Synthetic Commun.*, 12(10), 763–770 (1982)]. For example, a compound of Formula 1 is mixed with about an equimolar amount of trimethylsilyl cyanide and a Lewis Acid catalyst (such as $ZnI_2$, $AlCl_3$, or $BF_3$etherate; preferably $ZnI_2$), optionally with an aprotic solvent [such as dichloromethane, dichloroethane, ether, or THF ("tetrahydrofuran"); preferably dichloromethane]. The reaction takes place over a period of about 2 to 60 hours, preferably 4 to 40 hours, and most preferably about 16 hours. A temperature range of about −20° C. to 115° C., preferably 0° C. to 40° C., and most preferably about 20° C. is used. The intermediate of Formula 2 is isolated and purified in the usual manner.

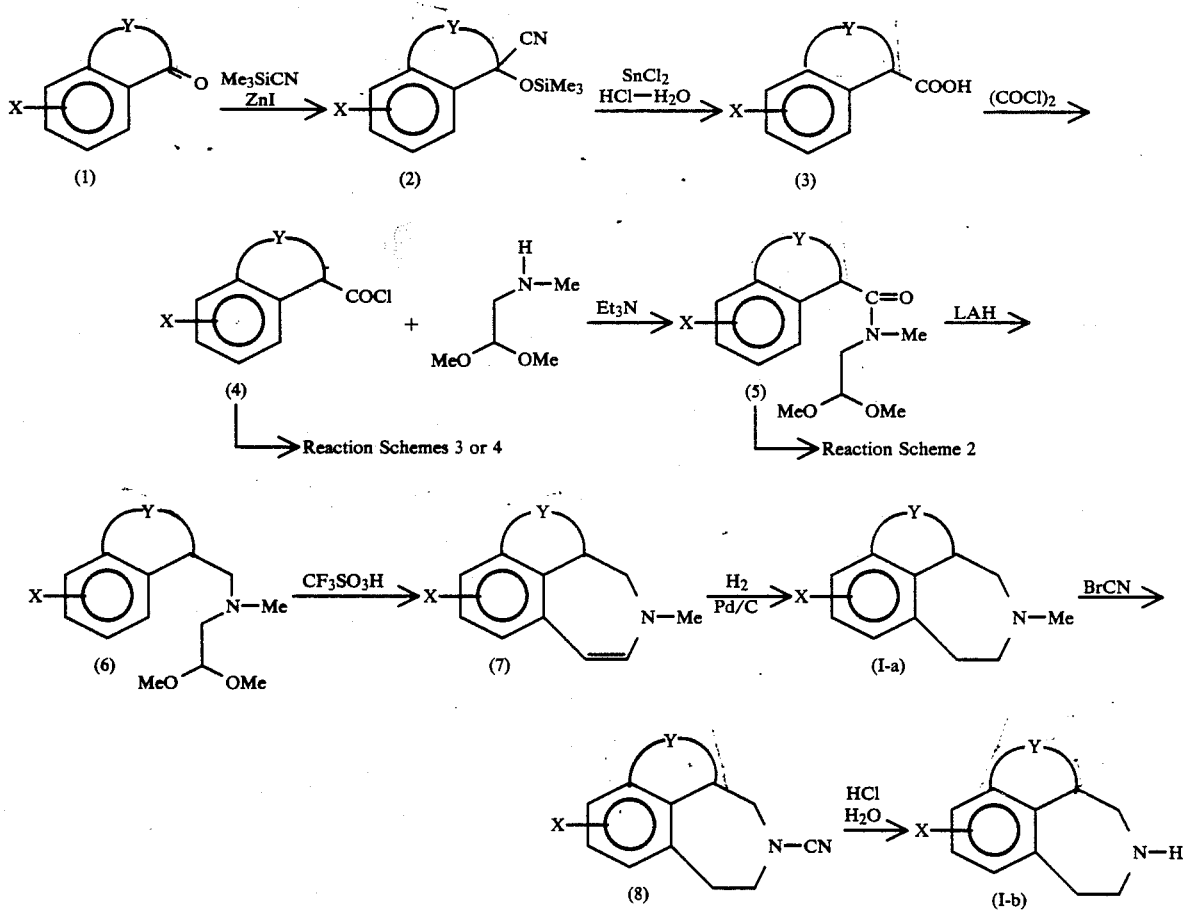

Reaction Scheme 1

-continued
Reaction Scheme 1

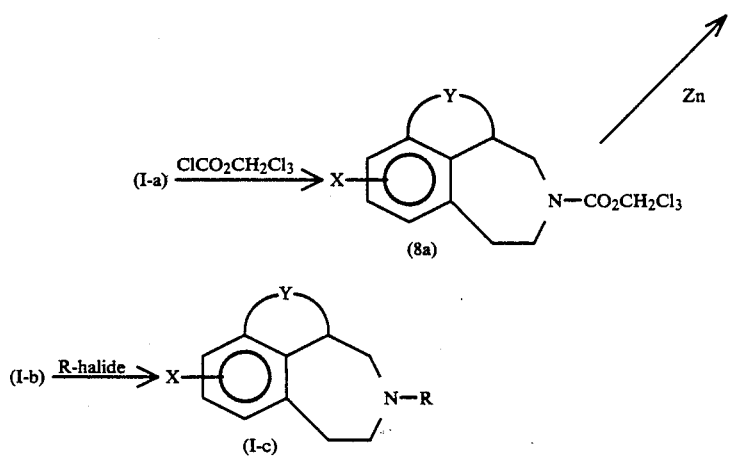

The compound of Formula 2 is dissolved in a protic solvent (such as an alkyl carboxylic acid; preferably acetic acid) reacted with an equimolar amount of stannous chloride in the presence of a small amount of an aqueous mineral acid (preferably concentrated HCl). The reaction takes place over a period of about 12 to 100 hours, preferably 12 to 48 hours, and most preferably about 24 hours. A temperature range of about 20° C. to 200° C., preferably 80° C. to 150° C., and most preferably about 120° C. is used. The intermediate of Formula 3 is isolated and purified in the usual manner.

Alternatively, for compounds of Formula I where Y has two carbons, an intermediate of Formula 3 can be prepared by first reacting indene with n-butyllithium and then quenching the resulting indenyllithium with carbon dioxide, according to the method of Cromwell, et al. [J. Am. Chem. Soc., 74, 4448–4449 (1952)] to give indane-carboxylic acid, which can be hydrogenated to give 1-indanecarboxylic acid (i.e., Formula 3 where Y is —CH$_2$—CH$_2$—).

PREPARATION OF INTERMEDIATE 4

A compound of Formula 3 (e.g., 6-methoxy-1-indanecarboxylic acid), optionally dissolved in an aprotic solvent (such as methylene chloride, tetrachloroethylene, ether, or- toluene; preferably methylene chloride), is reacted with a slight molar excess of a halide of a mineral or oxalic acid (such as oxalyl chloride, thionyl chloride, or phosphoryl chloride; preferably oxalyl chloride) in the presence of one drop of DMF ("dimethylformamide"). The reaction takes place over a period of about 15 minutes to 16 hours, preferably 30 minutes to 4 hours, and most preferably about 2 hours. A temperature range of about −20° C. to 100° C., preferably 0° C. to 50° C., and most preferably about 35° C. is used. The intermediate of Formula 4 is concentrated under vacuum and stirred for about 30 minutes, leaving the desired acid chloride in sufficiently pure form to be used for the next step.

PREPARATION OF INTERMEDIATE 5

A compound of Formula 4, dissolved in an aprotic solvent [such as methylene chloride, ether, or pyridine; preferably methylene chloride] and added dropwise to a stirred solution of an acetal of methylaminoacetaldehyde (preferably a slight molar excess of the dimethylactal of methylaminoacetaldehyde) in the presence of about 1 molar equivalent of triethylamine (itself dissolved in an aprotic solvent such as methylene chloride). The reaction takes place over a period of about 4 to 48 hours, preferably 4 to 24 hours, and most preferably about 16 hours. A temperature range of about −10° C. to 100° C., preferably 0° C. to 40° C., and most preferably about 20° C. is used. The amide of Formula 5 is then concentrated to a small volume, treated with ether and water, and the resulting organic layer washed with saturated sodium carbonate and sodium chloride. After drying, the ether solution is concentrated to yield the amide as an oil.

PREPARATION OF INTERMEDIATE 6

A compound of Formula 5 is dissolved in a polar but aprotic solvent (such as an ether, preferably diethylether or THF) followed by adding in excess of two molar equivalents of a reducing agent [such as lithium aluminum hydride ("LiAlH$_4$" or "LAH"), trimethoxylithium aluminum hydride, or BH$_3$.THF; preferably LAF, e.g., also in ether]. The reaction takes place over a period of about 1 to 48 hours, preferably 2 to 24 hours, and most preferably about 16 hours. A temperature range of about −20° C. to 60° C., preferably 0° C. to 40° C., and most preferably about 20° C. is used. The reaction mixture is treated dropwise with about 1 ml of water, 1 ml of a base (e.g., NaOH) and then 3 ml of water. Insoluble inorganic materials are removed by filtration and the filtrate is concentrated to give the aminoacetal of Formula 6, which is used without further purification.

PREPARATION OF INTERMEDIATE 7

A compound of Formula 6, optionally mixed with a halocarbon solvent such as methylene chloride, is treated slowly with a very strong acid, such as trifluoromethane sulfuric acid, with stirring. The reaction takes place over a period of about 1 to 48 hours, preferably 6 to 24 hours, and most preferably about 16 hours. A temperature range of about −10° C. to 120° C., preferably −10° C. to 40° C., and most preferably about 20° C. is used. The reaction is quenched with crushed ice and the resulting acid solution is extracted with ether to remove neutral materials. The remaining acid solution is made alkaline (e.g., by adding a base such as NaOH) and the desired intermediate of Formula 7 is extracted with ether.

PREPARATION OF FORMULA I WHERE R IS METHYL

A compound of Formula 7 is dissolved in an organic solvent optionally in the presence of an acid (such as an alcohol or THF; preferably ethanol with aqueous HCl) and subjected to catalytic hydrogenation (using $H_2$ and Ni, Pt or Pd; preferably $H_2$ and Pd/C or Pt/C as the catalyst). The reaction takes place over a period of about 15 minutes to 24 hours, preferably 30 minutes to 10 hours, and most preferably about 2 hours. A temperature range of about $-10°$ C. to $100°$ C., preferably $0°$ C. to $40°$ C., and most preferably about $20°$ C. is used. The catalyst is removed by filtration and the filtrate concentrated, followed by the addition of a base (such as aqueous NaOH) to yield the product compound of Formula I-a, as the free base.

PREPARATION OF INTERMEDIATE 8

A compound of Formula I where R is alkyl (e.g., Formula I-a where R is methyl) is dissolved in an inert solvent (such as toluene, carbon tetrachloride, or tetrachloroethylene; preferably toluene) and reacted with cyanogen bromide for about 30 minutes to 24 hours, preferably 2 to 16 hours, and most preferably about 4 hours. A temperature range of about $0°$ C. to $120°$ C., preferably about $50°$ C. is used. The intermediate of Formula 8 is isolated and purified in the usual manner.

PREPARATION OF INTERMEDIATE 8a

An alkylamine of Formula I (e.g., R=methyl) is dissolved in an inert solvent (such as benzene) and reacted with a slight molar excess of a stirred solution of trichloroethyl chloroformate. A small amount of potassium carbonate is then added and the mixture is heated to reflux. The progress of the reaction may be followed by TLC. When the conversion is substantially completed (about 30 minutes to 20 hours, preferably about 6 hours) the mixture is allowed to cool and is then filtered. The filtrate is then concentrated and the trichloroethyl carbamate intermediate of Formula 8a is isolated for use in the next step without purification.

PREPARATION OF FORMULA I WHERE R IS HYDROGEN

A compound of Formula 8 is dissolved in a protic solvent (such as a carboxylic acid, preferably acetic acid) and treated with an aqueous mineral acid (such as 20–37% HCl or 20–50% $H_2SO_4$; preferably concentrated HCl). The reaction takes place for about 4 to 40 hours, preferably about 24 hours. A temperature range of about $40°$ C. to $150°$ C., preferably about $100°$ C. is used. The product of Formula I-b is isolated and purified in the usual manner.

ALTERNATE PREPARATION OF FORMULA I WHERE R IS HYDROGEN

A compound of Formula 8a is dissolved (e.g., in a mixture of methanol and acetic acid; preferably from 5% acetic acid to 100% acetic acid, but not in the absence of acetic acid; most preferably 10–20% acetic acid in methanol). The solution is stirred at ambient temperature and Zinc dust is added in portions (a total of 5–10 g At. of zinc is used for each mole of the carbamate of Formula 8a). The mixture is then filtered, the filtrate is concentrated, and the remaining solid is chromatographed to yield the product of Formula I-b.

PREPARATION OF FORMULA I WHERE R IS ALKYL, ALKENYL, OR ARALKYL

A compound of Formula I-b is dissolved in a protic solvent or a polar aprotic solvent (such as ethanol, or DMF; preferably ethanol) and reacted with an alkyl halide, an alkenyl halide, or an aralkyl halide (such as ethyliodide, allyl bromide, prop-2-enylchloride, and benzyl chloride; depending on what is desired as R). The reaction takes place for about 1 to 48 hours, preferably 2 to 16 hours, and most preferably about 16 hours. A temperature range of about $0°$ C. to $120°$ C., preferably $-20°$ C. to $100°$ C., and most preferably about $65°$ C. to $80°$ C. is used. The product of Formula I-c is isolated and purified in the usual manner.

FIRST ALTERNATIVE PREPARATION OF FORMULA I-a

This first alternative preparation is illustrated in Reaction Scheme 2, which follows.

PREPARATION OF INTERMEDIATE 9

A compound of Formula 5 is dissolved in a protic solvent (such as a carboxylic acid, preferably acetic acid) and treated with an aqueous mineral acid (such as HCl, HBr, or $H_2SO_4$; preferably concentrated HCl). The reaction takes place for about 15 minutes to 24 hours, preferably about 1 to 16 hours, and most

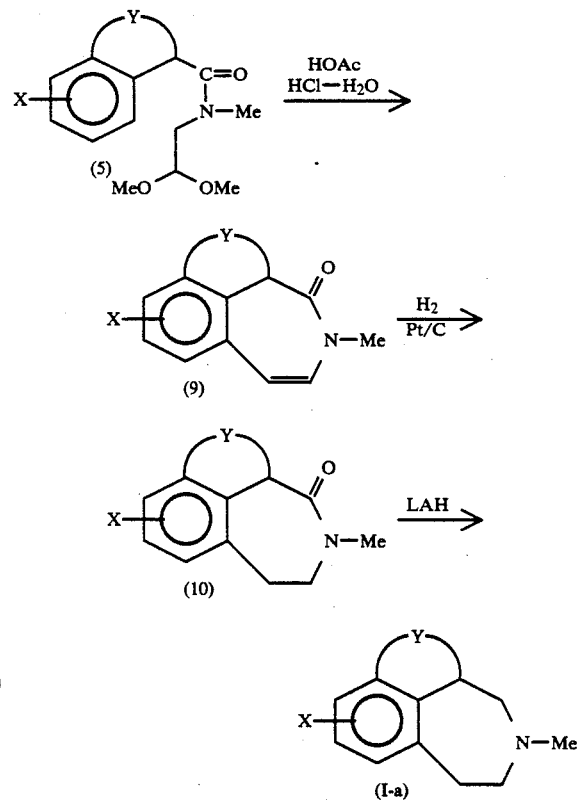

Reaction Scheme 2 preferably about 6 hours. A temperature range of about $20°$ C. to $200°$ C., preferably about $60°$ C. to $120°$ C., and most preferably about $80°$ C. is used. The reaction is quenched over ice and extracted with ether. The ether extract is made alkaline with, e.g., saturated sodium bicarbonate, dried, filtered and concentrated to yield the intermediate of Formula 9, which is used without further purification.

PREPARATION OF INTERMEDIATE 10

A compound of Formula 9 is dissolved in an organic solvent (such as a lower alcohol; preferably ethanol), optionally in the presence of an acid, and subjected to catalytic hydrogenation (using $H_2$ and Ni, Pt or Pd; preferably $H_2$ and Pt/C as the catalyst). The reaction takes place over a period of about 2 to 60 hours, preferably 4 to 48 hours, and most preferably about 24 hours. A temperature range of about $-10°$ C. to $80°$ C., preferably $0°$ C. to $40°$ C., and most preferably about $20°$ C. is used. The catalyst is removed by filtration and the filtrate concentrated, followed by the addition of a base (such as aqueous NaOH) to yield the lactam intermediate compound of Formula 10, which is used without further purification in the following preparation, or in Preparation 17.

PREPARATION OF FORMULA I WHERE R IS METHYL

A compound of Formula 10 is dissolved in an aprotic solvent (such as an ether, preferably diethylether or THF) followed by adding in excess of two molar equivalents of a reducing agent (such a hydride of aluminum or boron; preferably LAH or $BH_3$.THF; preferably LAH, e.g., also in ether). The reaction takes place over a period of about 1 to 60 hours, preferably 4 to 48 hours, and most preferably about 24 hours. A temperature range of about $-20°$ C. to $50°$ C., preferably $0°$ C. to $50°$ C., and most preferably about $20°$ C. is used. The reaction mixture is worked up in the usual manner (aqueous). Insoluble inorganic materials are removed by filtration and the filtrate concentrated to give the product compound of Formula I-a, as the free base.

SECOND ALTERNATIVE PREPARATION OF FORMULA I-a

This second alternative preparation is illustrated in Reaction Scheme 3, which follows.

PREPARATION OF INTERMEDIATE 11

A compound of Formula 4 is dissolved in an aprotic solvent (such as a halocarbon or an ether; preferably methylene chloride) and added slowly to a stirred solution of in excess of two molar equivalents of an aminoalkanol [such as 2-(methylamino)ethanol]. Alternatively, one molar equivalent of the aminoalkanol can be used plus another base. The reaction takes place Reaction Scheme 3

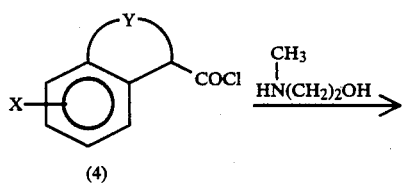

(4)

-continued
Reaction Scheme 3

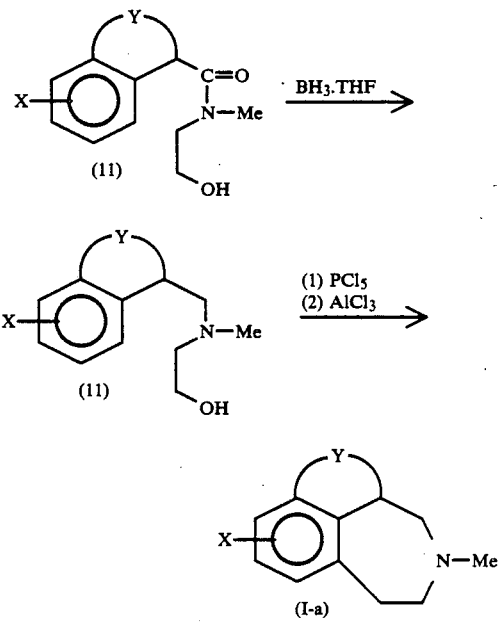

over a period of about 5 minutes to 24 hours, preferably about 30 minutes. A temperature range of about $-40°$ C. to $80°$ C., preferably $20°$ C. to $40°$ C., and most preferably about $0°$ C. is used. Water is added and the organic layer is then washed, e.g., with a dilute acid, water, saturated $NaHCO_3$ and saturated NaCl. The intermediate of Formula 11 is then dried, concentrated and used without further purification.

PREPARATION OF INTERMEDIATE 12

A compound of Formula 11 is dissolved in an aprotic solvent (such as an ether, preferably diethylether or THF) followed by adding an excess of a reducing agent (such a borane or a metal hydride; preferably LAH, $BH_3$.THF or $BH_3$.$(CH_3)_2$S; preferably $BH_3$.THF). The reaction takes place over a period of about 10 minutes to 24 hours, preferably 10 minutes to 16 hours, and most preferably about 30 minutes. A temperature range of about $0°$ C. to $100°$ C., preferably $0°$ C. to $80°$ C., and most preferably about $65°$ C. is used. The reaction mixture is worked up in the usual manner (aqueous). Insoluble inorganic materials are removed by filtration and the filtrate concentraed to give the intermediate of Formula 12, which is used without further purification.

PREPARATION OF FORMULA I WHERE R IS METHYL

A compound of Formula 12 is dissolved in a high-boiling, aprotic solvent (such as trichlorobenzene, nitrobenzene, or tetrachloroethylene; preferably trichlorobenzene) followed by adding slightly less than half a molar equivalent of a phosphorous chloride (such as phosphorous oxychloride, phosphorous trichloride, or phosphorous pentachloride; preferably phosphorous pentachloride). The mixture is then heated to between about $80°$ C. and $150°$ C., preferably about $110°$ C., and about two molar equivalents of a metal chloride (such as aluminum chloride) is added slowly (over a period of about 15 minutes to 1 hour, preferably about 30 minutes). The temperature is then increased to between about 150° C. and 250° C., preferably about 200° C. and the mixture is stirred for an additional 1 to 8 hours, preferably about 3 hours. The reaction mixture is allowed to cool to about 60° C. to 100° C., preferably about 80° C., and acidified, for example by adding 12% HCl. Toluene is added and the organic layers are separated. The remaining aqueous phase is made alkaline by the addition of a base (e.g., 50% NaOH) and the product is extracted with ethyl acetate, which is then evaporated and the remaining crude product purified by conventional means to yield the product compound of Formula I-a, as the free base.

THIRD ALTERNATIVE PREPARATION OF FORMULA I-a AND I-d

This third alternative preparation is illustrated below in Reaction Scheme 4.

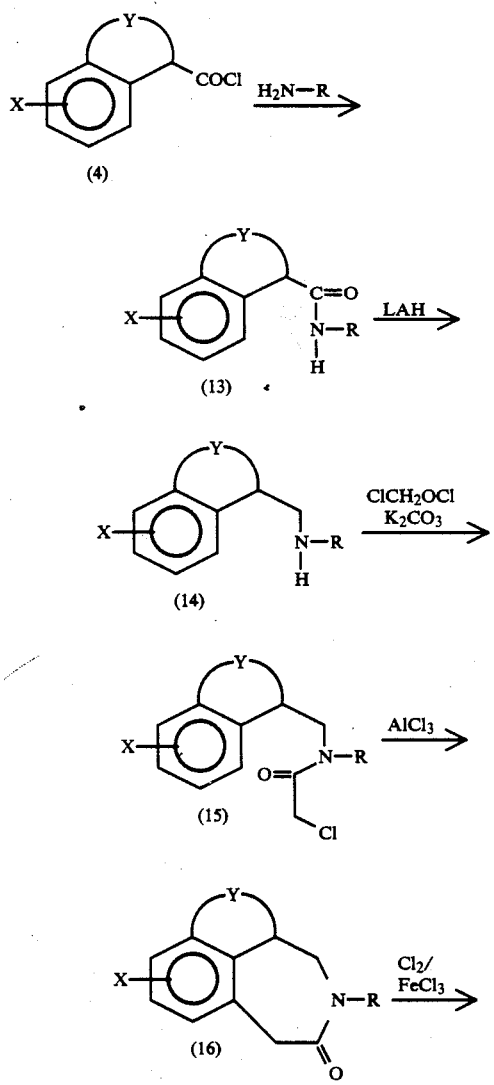

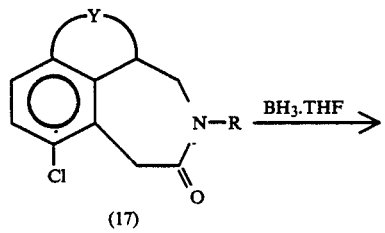

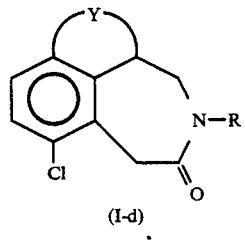

PREPARATION OF INTERMEDIATE 13

A compound of Formula 4 is dissolved in a solvent (such as ether, ethylacetate, or methylene chloride; preferably ethylacetate) and added slowly to an excess of a stirred, ice bath-cooled solution of an amine, such as 40% aqueous methylamine or N-propylamine. The reaction takes place for about 1 to 48 hours, preferably about 1 to 16 hours, and most preferably about 4 hours. A temperature range of about 0° C. to 80° C., preferably about 0° C. to 40° C., and most preferably about 0° C. to 20° C. is used. The organic layer is separated, washed and evaporated to give the intermediate of Formula 13, which is used without further purification.

PREPARATION OF INTERMEDIATE 14

A compound of Formula 13 is dissolved in an aprotic solvent (such as an ether, preferably diethylether or THF; most preferably an ether-THF mixture) and slowly added to in excess of two molar equivalents of a reducing agent (such a hydride of aluminum or boron; preferably LAH, BH$_3$.THF, or BH$_3$.Me$_2$S; most preferably LAH). The reaction takes place over a period of about 1 to 48 hours, preferably 1 to 16 hours, and most preferably about 6 hours. A temperature range of about 0° C. to 80° C., preferably 60° C. is used. The reaction mixture is digested by treating dropwise with water, a base (e.g., NaOH) and then water. The intermediate of Formula 14 is used without further purification.

PREPARATION OF INTERMEDIATE 15

A compound of Formula 14 is dissolved in a two-phase solvent system (such as water and ethylacetate, ether or methylene chloride; preferably water and ethylacetate) in the presence of an acid scavenger (such as potassium carbonate). The mixture is stirred over an ice bath and a molar equivalent of an acylating agent (such as chloroacetylchloride) is added slowly. The reaction takes place for about 30 minutes to 16 hours, preferably about 1 to 6 hours, and most preferably about 1.5 hours. A temperature range of about −10° C. to 80° C., preferably about 0° C. to 30° C., and most preferably about 5° C. to 20° C. is used. The organic layer is separated, and concentrated to give the intermediate of Formula 15, which is used without further purification.

PREPARATION OF INTERMEDIATE 16

Intermediate 16 is prepared by introducing a compound of Formula 15 into in excess of two molar equivalents of a Friedel-Crafts catalyst (such as AlCl₃, AlBr₃ or SnCl₄; preferably AlCl₃) dissolved in a high-boiling halocarbon solvent (such as trichlorobenzene or tetrachloroethylene; preferably trichlorobenzene), preheated to about 80° C. to 180° C., preferably about 80° C. to 150° C., and most preferably about 110° C. The reaction takes place for about 2 to 7 hours, preferably about 5 hours, and is then quenched and extracted to give the intermediate of Formula 16. This can be reduced as described in Reaction Scheme 2, as described below, or when X is represents $R^1$, $R^2$ and $R^3$ being hydrogen, Formula 16 can be converted to a halo-substituted benzene compound, illustrated as the 5-chloro compound of Formula 17.

PREPARATION OF INTERMEDIATE 17

A product of Formula 16 can be halogenated by dissolving it in a polar solvent (such as acetonitrile or a acetic acid; preferably acetonitrile) optionally in the presence of water, and reacting it with chlorine or a source of chloride ion (such as N-chlorosuccinimide) in the presence of FeCl₃. The reaction takes place for about 1 to 48 hours, preferably about 1 to 24 hours, and most preferably about 6 hours. A temperature range of about −10° C. to 50° C., preferably about 0° C. to 20° C. is used. The reaction mixture is concentrated and treated with ether and water to give the intermediate of Formula 17, e.g., shown where $R^3$ is chloro, which is used without further purification.

PREPARATION OF FORMULA I WHERE R IS METHYL, $R^1$ AND $R^2$ ARE HYDROGEN, AND $R^3$ IS HYDROGEN OR CHLORO

A compound of Formula 16 or Formula 17 is dissolved in an aprotic solvent (such as an ether, preferably diethylether or THF) followed by adding in excess of two molar equivalents of a reducing agent (such as hydride of aluminum or boron; preferably LAH, BH₃.THF, or NaBH₄.transition metal chloride; most preferably BH₃.THF). The reaction takes place over a period of about 1 to 48 hours, preferably 1 to 24 hours, and most preferably about 16 hours. A temperature range of about −10° C. to 60° C., preferably 0° C. to 40° C., and most preferably about 20° C. is used. The reaction mixture is treated dropwise with methanol and the solvents removed under vacuum. The residue is treated with a dilute acid (such as HCl) and digested on a steam bath for about 3 hours. After cooling, the aqueous solution is washed with ether, made alkaline with a base (such as NaOH) and extracted with ether. The ether extract is concentrated to give the product compound of Formula I where R is Methyl, and X is hydrogen or chloro, as the free base, yielding Formula I-a from Formula 16 and yielding Formula I-d from Formula 17.

SALTS OF COMPOUNDS OF FORMULA I

Some of the compounds of Formula I may be converted to corresponding acid addition salts. The conversion is accomplished by treatment with a stoichiometric amount of an appropriate acid, such as hydrochloric acid, sulfuric acid, methanesulfonic acid, HBr, or the like. Typically, the free base is dissolved in a polar organic solvent such as ethanol or methanol, and the acid added in water, ethanol or methanol. The temperature is maintained at 0°-50° C. The resulting salt precipitates spontaneously or may be brought out of solution with a less polar solvent.

The acid addition salts of the compounds of Formula I may be decomposed to the corresponding free bases by treating with an excess of a suitable base, such as ammonia or sodium bicarbonate, typically in the presence of aqueous solvent, and at a temperature of between 0° and 50° C. The free base form is isolated by conventional means, such as extraction with an organic solvent.

PREFERRED COMPOUNDS

The compounds of Formula I where Y has two or three carbon atoms are preferred. Also, those compounds where R is alkyl, particularly methyl, are preferred. Similarly preferred are those compounds where $R^1$ and $R^2$ are hydrogen and $R^3$ is not hydrogen, particularly where $R^3$ is chloro or methoxy. The salts of Formula I are also preferred, especially the HCl and HBr salts.

Particularly preferred are the compounds of Formula I where:
R is methyl, $R^3$ is chloro and Y is —(CH₂)₂—; and
R is methyl, $R^3$ is methoxy and Y is —(CH₂)₃—.

Most preferred is the compound of Formula I where R is methyl, $R^1$ and $R^2$ are hydrogen, $R^3$ is chloro and Y is —(CH₂)₃—, especially the HCl salt, i.e., 2-methyl-5-chloro-1,3,4,8,9,10,10a-octahydro-2H-naphth[1,8-cd]azepine hydrochloride.

PREFERRED PROCESSES

The compounds of the present invention can be prepared according to the following last steps:

contacting a 2-methyl-optionally-5-, 6- and/or 7-substituted-1,8,9,10,11,11a-hexahydro-2H-cyclohepta[c,d][3]-benzazepine with an acid in the presence of a catalyst to yield the corresponding 2-methyl-optionally-5-, 6- and/or 7-substituted-1,3,4,8,9,10,11,11a-octahydro-2H-cyclohepta[c,d][3]benzazepine;

contacting a 2-methyl-optionally-5-, 6- and/or 7-substituted-1,8,9,10,10a-hexahydro-2H-naphth[1,8-cd]azepine with an acid in the presence of a catalyst to yield the corresponding 2-methyl-optionally- 5-, 6- and/or 7-substituted-1,2,3,4,8,9,10,10a-octahydronaphth[1,8-cd]azepine;

contacting a 2-methyl-optionally-5-, 6- and/or 7-substituted-1,8,9,9a-tetrahydro-2H-indeno[1,7-cd]-azepine with an acid in the presence of a catalyst to yield the corresponding 2-methyl-optionally- 5-, 6- and/or 7-substituted-1,3,4,8,9,9a-hexahydro-2H-indeno[1,7-cd]azepine;

contacting a 2-cyano-optionally- 5-, 6- and/or 7-substituted-1,3,4,8,9,10,11,11a-octahydro-2H-cyclohepta[c,d][3]benzazepine with an acid to yield the corresponding optionally-5-, 6- and/or 7-substituted-1,3,4,8,9,10,11,11a-octahydro-2H-cyclohepta[c,d][3-]benzazepine;

contacting a 2-cyano-optionally- 5-, 6- and/or 7-substituted-1,2,3,4,8,9,10,10a-octahydronaphth[1,8-cd]azepine with an acid to yield the corresponding optionally-5-, 6- and/or 7-substituted-1,2,3,4,8,9,10,10a-octahydronaphth[1,8-cd]azepine;

contacting a 2-cyano-optionally- 5-, 6- and/or 7-substituted-1,3,4,8,9,9a-hexahydro-2H-indeno[1,7-cd]azepine with an acid to yield the corresponding optionally-5-, 6- and/or 7-substituted-1,3,4,8,9,9a-hexahydro-2H-indeno[1,7-cd]azepine;

contacting a 2-trichloroethylcarbamoyl-optionally-5-, 6- and/or 7-substituted-1,3,4,8,9,10,11,11a-octahydro-2H-cyclohepta[c,d][3]benzazepine with zinc dust to yield the corresponding optionally-5-, 6- and/or 7-substituted-1,3,4,8,9,10,11,11a-octahydro-2H-cyclohepta[c,d][3]benzazepine;

contacting a 2-trichloroethylcarbamoyl-optionally-5-, 6- and/or 7-substituted-1,2,3,4,8,9,10,10a-octahydro-2H-naphth[1,8-cd]azepine with zinc dust to yield the corresponding optionally-5-, 6- and/or 7-substituted-1,2,3,4,8,9,10,10a-octahydronaphth[1,8-cd]azepine;

contacting a 2-trichloroethylcarbamoyl-optionally-5-, 6- and/or 7-substituted-1,3,4,8,9,9a-hexahydro-2H-indeno[1,7-cd]azepine with zinc dust to yield the corresponding optionally-5-, 6- and/or 7-substituted-1,3,4,8,9,9a-hexahydro-2H-indeno[1,7-cd]azepine;

contacting an optionally-5-, 6- and/or 7-substituted-1,3,4,8,9,10,11,11a-octahydro-2H-cyclohepta[c,d][3]benzazepine with an alkenyl-halide to yield the corresponding 2-alkyl-optionally-5-, 6- and/or 7-substituted-1,3,4,8,9,10,11,11a-octahydro-2H-cyclohepta[c,d][3]benzazepine;

contacting an optionally-5-, 6- and/or 7-substituted-1,2,3,4,8,9,10,10a-octahydronaphth[1,8-cd]azepine with an alkenyl-halide to yield the corresponding 2-alkyl-optionally-5-, 6- and/or 7-substituted-1,2,3,4,8,9,10,10a-octahydronaphth[1,8-cd]azepine;

contacting an optionally-5-, 6- and/or 7-substituted-1,3,4,8,9,9a-hexahydro-2H-indeno[1,7-cd]azepine with an alkenyl-halide to yield the corresponding 2-alkyl-optionally-5-, 6- and/or 7-substituted-1,3,4,8,9,9a-hexahydro-2H-indeno[1,7-cd]azepine;

contacting a 1-oxo-2-methyl-optionally- 5-, 6- and/or 7-substituted-1,3,4,8,9,10,11,11a-octahydro-2H-cyclohepta[c,d][3]benzazepine with a reducing agent to yield the corresponding 2-methyl-optionally-5-, 6- and/or 7-substituted-1,3,4,8,9,10,11,11a-octahydro-2H-cyclohepta[c,d][3]benzazepine;

contacting a 1-oxo-2-methyl-optionally- 5-, 6- and/or 7-substituted-1,2,3,4,8,9,10,10a-octahydronaphth[1,8-cd]azepine with a reducing agent to yield the corresponding 2-methyl-optionally-5-, 6- and/or 7-substituted-1,2,3,4,8,9,10,10a-octahydronaphth[1,8-cd]azepine;

contacting a 1-oxo-2-methyl-optionally- 5-, 6- and/or 7-substituted-1,3,4,8,9,9a-hexahydro-2H-indeno[1,7-cd]azepine with a reducing agent to yield the corresponding 2-methyl-optionally-5-, 6- and/or 7-substituted-1,3,4,8,9,9a-hexahydro-2H-indeno[1,7-cd]azepine;

contacting a 1-[N-(2-hydroxyethyl)methylaminomethyl]benzosubarane with a phosphorous chloride and a metal halide to yield the corresponding 2-methyl-optionally-5-, 6- and/or 7-substituted-1,3,4,8,9,10,11,11a-octahydro-2H-cyclohepta[c,d][3]benzazepine;

contacting a 1-[N-(2-hydroxyethyl)methylaminomethyl]-1,2,3,4-tetrahydronaphthalene with a phosphorous chloride and a metal halide to yield the corresponding 2-methyl-optionally-5-, 6- and/or 7-substituted-1,2,3,4,8,9,10,10a-octahydronaphth[1,8-cd]azepine;

contacting a 1-[N-(2-hydroxyethyl)methylaminomethyl]indane with a phosphorous chloride and a metal halide to yield the corresponding 2-methyl-optionally-5-, 6- and/or 7-substituted-1,3,4,8,9,9a-hexahydro-2H-indeno[1,7-cd]azepine;

contacting a 2-methyl-3-oxo-optionally- 5-, 6- and/or 7-substituted-1,3,4,8,9,10,11,11a-octahydro-2H-cyclohepta[c,d][3]benzazepine with a reducing agent to yield the corresponding 2-methyl-optionally-5-, 6- and/or 7-substituted-1,3,4,8,9,10,11,11a-octahydro-2H-cyclohepta[c,d][3]benzazepine;

contacting a 2-methyl-3-oxo-optionally- 5-, 6- and/or 7-substituted-1,2,3,4,8,9,10,10a-octahydronaphth[1,8-cd]azepine with a reducing agent to yield the corresponding 2-methyl-optionally-5-, 6- and/or 7-substituted-1,2,3,4,8,9,10,10a-octahydronaphth[1,8-cd]azepine;

contacting a 2-methyl-3-oxo-optionally- 5-, 6- and/or 7-substituted-1,3,4,8,9,9a-hexahydro-2H-indeno[1,7-cd]azepine with a reducing agent to yield the corresponding 2-methyl-optionally-5-, 6- and/or 7-substituted-1,3,4,8,9,9a-hexahydro-2H-indeno[1,7-cd]azepine;

contacting a 5-chloro-2-methyl-3-oxo-1,3,4,8,9,10,11,11a-octahydro-2H-cyclohepta[c,d][3]benzazepine with a reducing agent to yield the corresponding 5-chloro-2-methyl-1,3,4,8,9,10,11,11a-octahydro-2H-cyclohepta[c,d][3]benzazepine;

contacting a 5-chloro-2-methyl-3-oxo-1,2,3,4,8,9,10,10a-octahydronaphth[1,8-cd]azepine with a reducing agent to yield the corresponding 5-chloro-2-methyl-1,2,3,4,8,9,10,10a-octahydronaphth[1,8-cd]azepine;

contacting a 5-chloro-2-methyl-3-oxo-1,3,4,8,9,9a-hexahydro-2H-indeno[1,7-cd]azepine with a reducing agent to yield the corresponding 5-chloro-2-methyl-1,3,4,8,9,9a-hexahydro-2H-indeno[1,7-cd]azepine;

contacting a pharmaceutically acceptable acid with a compound of Formula I to form the corresponding acid addition salt of Formula I;

substituting a pharmaceutically acceptable acid salt of Formula I with another pharmaceutically acceptable acid; and contacting an acid addition salt of Formula I with a base to form the corresponding free base compounds of Formula I.

UTILITY AND ADMINISTRATION

General Utility

The compounds of the present invention, including the pharmaceutically acceptable salts thereof, and the compositions containing them, are useful as CNS agents, including such uses as antidepressants, anxiolytics and antihypertensives in mammals, whether domestic (cattle, pigs, sheep, goats, horses), pets (cats, dogs), or preferably humans. These utilities are associated with binding to $\alpha_2$ and 5-HT$_{1A}$ receptors. The compounds can be used both prophylactically (e.g., to prevent allograft rejection) and therapeutically.

Testing

In vitro testing for $\alpha_2$ activity is done, for example, using an $\alpha_2$ binding affinity assay, as described by Clark, et al., *J. Med. Chem.*, 26 855 (1983), or as described by Cheung, et al., *Europ. J. Pharmacol.*, 84 79–85 (1982).

In vitro testing for 5-HT$_{1A}$ activity is done, for example, using a modification of the 5-HT$_{1A}$ binding affinity assay, as described by Gozlan, et al., *Nature*, 305 140–142 (1983) or Norman et al., *Mol. Pharmacol.*, 28 487 (1986). The use of 8-OH-DPAT in such assays has been described by Peroutka and Demopulos, *Europ. J. Pharmacol.*, 199–200 (1986).

In vivo testing to demonstrate the described activity of the present compounds is done by the reversal of 8-OH DPAT effects in rodents method, described by Tricklebank, et al., *Europ. J. Pharmacol.*, 106 271–282 (1984).

GENERAL ADMINISTRATION

Administration of the active compounds of Formula I, in pure form or in an appropriate pharmaceutical composition can be carried out via any of the accepted modes of administration of agents for serving similar utilities. Thus, administration can be, for example, orally, nasally, parenterally or topically, in the form of solid, semi-solid or liquid dosage forms, such as for example, tablets, suppositories, pills, capsules, powders, solutions, suspensions, emulsions, creams, lotions, aerosols, ointments or the like, preferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc.

Generally, depending on the intended mode of administration, the pharmaceutically acceptable compositions will contain about 1% to about 99% by weight of the pharmaceutically active compound of this invention and 99% to 1% by weight of suitable pharmaceutical excipients. Preferably, the composition will be about 5 to 75% by weight of a pharmaceutically active compound, with the rest being suitable pharmaceutical excipients.

The preferred manner of administration, for the conditions detailed above, is oral using a convenient daily dosage regimen which can be adjusted according to the degree of affliction. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, gum acacia, polyvinylpyrrolidone, gelatin, cellulose and derivatives thereof, and the like.

The active compounds of Formulas I may be formulated into a suppository using, for example, about 0.5% to about 50% active ingredient disposed in a carrier of polyethylene glycols (PEG) [e.g., PEG 1000 (96%) and PEG 4000 (4%)].

Liquid pharmaceutically administerable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see *Remington's Pharmaceutical Sciences*, 16th Ed., (Mack Publishing Company, Easton, Pa., 1980). The composition to be administered will, in any event, contain a quantity of the active compound(s) in a pharmaceutically effective amount for relief of the particular condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of an active compound of Formula I. Most conditions respond to treatment comprising a dosage level on the order of 0.4 to 30 mg/kg of body weight per day, and most preferably about 10 mg/kg/day. Thus, for administration to a 70 kg person, the dosage range would be about 7.0 mg to 7 g per day, preferably about 28.0 mg to 2.1 g per day.

EXAMPLES

The following preparations and examples are given to enable those skilled in the art to more clearly understand and to practice the present invention. They should not be considered as a limitation on the scope of the invention, but merely as being illustrative and representative thereof.

PREPARATION 1

1A. Formula 2 Where X is 6—OCH$_3$, and Y is —(CH$_2$)$_3$—

As described with reference to Reaction Scheme I, compounds of Formula I can be converted to the intermediates of Formula 2 according to the procedure described by Belletire, et al. [*Synthetic Commun.*, 12(10), 763–770 (1982)]. For example, to a 50 ml single neck round bottom reaction flask equipped with a magnetic stirrer, a 50 ml pressure equalizing addition funnel and a nitrogen inlet, is added 10.5 g (56.7 mmol) of 6-methoxy-1-tetralone and 0.35 g of ZnI$_2$. The addition funnel is charged with trimethylsilylcyanide, 19.0 g (191 mmol) and the reaction apparatus flushed with dry nitrogen. With vigorous stirring the trimethylsilylcyanide is added over a 5' period. The reaction mixture is stirred at room temperature for 48 hours. 1-Cyano-1-trimethylsiloxy-6-methoxy-1,2,3,4-tetrahydronaphthalene, an intermediate of Formula 2, is isolated and purified in the usual manner.

1B. Formula 2 Varying X and Y

By following the procedure of part A and substituting for 6-methoxy-1-tetralone the following:

6-methoxy-1-indanone,
1-indanone,
1-tetralone,
4,6-dimethoxy-1-tetralone,
4,5,6-trichloro-1-tetralone,
6-chloro-1-benzosuberone, and
1-benzosuberone;

there are obtained the following respective compounds:
1-cyano-1-trimethylsiloxy-6-methoxy-indane,
1-cyano-1-trimethylsiloxy-indane,
1-cyano-1-trimethylsiloxy-1,2,3,4-tetrahydronaphthylene,
1-cyano-1-trimethylsiloxy-4,6-dimethoxy-1,2,3,4-tetrahydronaphthalene, 1-cyano-1-trimethylsiloxy-4,5,6-trichloro-1,2,3,4-tetrahydronaphthalene,
1,2-benzo-6-chloro-7-cyano-7-trimethylsiloxycycloheptane, and
1,2-benzo-7-cyano-7-trimethylsiloxy-cycloheptane.

PREPARATION 2

2A. Formula 3 Where X is 6—$OCH_3$, and Y is —$(CH_2)_3$—

As described with reference to Reaction Scheme I, compounds of Formula 2 can be converted to the intermediates of Formula 3 according to the procedure described by Belletire, et al. [*Synthetic Commun.*, 12(10), 763–770 (1982)]. For example, to a 250 ml single neck round bottom reaction flask equipped with a magnetic stirrer, reflux condenser and nitrogen inlet, is added 6.0 g (21.79 mmol) of 1-cyano-1-trimethylsiloxy-6-methoxy-1,2,3,4-tetrahydronaphthalene. In one portion, 20.0 g (88.6 mmol) stannous chloride decahydrate followed by 20 ml glacial acetic acid and 20 ml concentrated hydrochloric acid is added. The reaction apparatus is immediately flushed with nitrogen and plunged into a preheated (140° C.) oil bath. With vigorous stirring the reaction mixture is heated at reflux for 65 hours, cooled to room temperature, diluted with 250 ml chloroform, the layers separated, and the aqueous layer again extracted with chloroform. The combined organic layers are extracted three times with 2N aqueous KOH, and the combined basic aqueous layers back-extracted with ether. The basic aqueous layer is acidified with ice-bath cooling, extracted three times with chloroform, the organic layers dried over magnesium sulfate, filtered, and the volatiles removed to give 6-methoxy-1,2,3,4-tetrahydronaphthalene-1-carboxylic acid, an intermediate of Formula 3, as a crystalline solid.

2B. Formula 3 Varying X and Y

By following the procedure of part A and substituting for 1-cyano-1-trimethylsiloxy-6-methoxy-1,2,3,4-tetrahydronaphthalene the following:
1-cyano-1-trimethylsiloxy-6-methoxy-indane,
1-cyano-1-trimethylsiloxy-indane,
1-cyano-1-trimethylsiloxy-1,2,3,4-tetrahydronaphthylene,
1-cyano-1-trimethylsiloxy-4,6-dimethoxy-1,2,3,4-tetrahydronaphthalene,
1-cyano-1-trimethylsiloxy-4,5,6-trichloro-1,2,3,4-tetrahydronaphthalene,
1,2-benzo-6-chloro-7-cyano-7-trimethylsiloxycycloheptane, and
1,2-benzo-7-cyano-7-trimethylsiloxy-cycloheptane;
there are obtained the following respective compounds:
6-methoxy-indane-1-carboxylic acid,
indane-1-carboxylic acid,
1,2,3,4-tetrahydronaphthalene-1-carboxylic acid,
4,6-dimethoxy-1,2,3,4-tetrahydronaphthalene-1-carboxylic acid,
4,5,6-trichloro-1,2,3,4-tetrahydronaphthalene-1-carboxylic acid,
1,2-benzo-6-chloro-cycloheptane-1-carboxylic acid, and
1,2-benzo-cycloheptane-1-carboxylic acid.

PREPARATION 3

3A. Formula 3 Where X is 6-Chloro, and Y is —$(CH_2)_2$—

Compounds of Formula 3 can be halogenated according to the procedure described by Tetsuya, et al. [*Chem. Pharm. Bull.*, 25(12), 3198–3209 (1977)]. For example, to a stirred, ice-cooled mixture of indane-1-carboxylic acid 0.81 g (5 mmol) and 5 mmol of $FeCl_3$ dissolved in 5 ml of acetonitrile, is added dropwise a solution of 0.53 g (7.5 mmol) of $Cl_2$ in 7 ml of acetonitrile. The mixture is stirred for 1.3 hours under cooling and then poured onto ice-water. The mixture is extracted with ether and the extract washed with water, dried over anhydrous $MgSO_4$ and concentrated under reduced pressure. The residue is treated with bis(trimethylsilyl)acetamide giving predominantly 6-chloro-indane-1-carboxylic acid.

3B. Formula 3 Where X is 4-Chloro, and Y is —$(CH_2)_2$—

By following the procedure of Tetsuya, et al. referenced in part A, the 4-chloro compound can be obtained. For example, in a nitrogen atmosphere, to a stirred, ice-cooled mixture of 0.81 g (5 mmol) indane-1-carboxylic acid in 30 ml of methylene chloride is added 0.9 g (5 mmol) of $TiCl_4$. To this mixture is added dropwise a solution of 0.87 g (5 mmol) of m-chloroperbenzoic acid in 5 ml of methylene chloride, over a period of 20 minutes. The mixture is stirred for 5 hours at room temperature and then poured onto ice-water. The mixture is extracted with methylene chloride and the extract washed with water, dried over anhydrous $MgSO_4$ and concentrated under reduced pressure. The residue is treated with bis(trimethylsilyl)acetamide giving about 53% 6-chloro-indane-1-carboxylic acid and 37% 4-chloro-indane-1-carboxylic acid, which are separated by conventional means.

3C. Formula 3 Where X is 6-Bromo, and Y is —$(CH_2)_2$—

By following the procedure of Tetsuya, et al. referenced in part A, the 6-bromo compound can be obtained. For example, to a stirred, ice-cooled mixture of 8.1 g (50 mmol) indane-1-carboxylic acid and 8.1 g of $FeCl_3$ in 300 ml of $CCl_4$ is added dropwise a solution of 8.8 g of $Br_2$ in 100 ml methylene chloride over a 1 hour period. The mixture is stirred for 3 hours under cooling and then for 1.5 hours at room temperature. The mixture is poured into 500 ml of dilute HCl and extracted with $CHCl_3$. The extract is washed with water, dried over anhydrous $MgSO_4$ and concentrated under reduced pressure. The residue is crystallized from hexane to give 6-bromo-indane-1-carboxylic acid.

3D. Formula 3 Where X is Nitro, and Y is —$(CH_2)_2$—

By following the procedure of Tetsuya, et al. referenced in part A, the 4-nitro and 6-nitro compounds can be obtained. For example, to a stirred solution of 1.5 g indane-1-carboxylic acid in 20 ml of acetic anhydride is added at −5° C. a mixture of 4 ml $HNO_3$ and 8 ml of acetic anhydride. The mixture is stirred for 1.5 hours at −5° C. and then poured onto ice-water. The mixture is extracted with ether. The extract is washed with water, dried over anhydrous $MgSO_4$ and evaporated under reduced pressure to give a mixture of 6-nitro-indane-1-carboxylic acid and 4-nitro-indane-1-carboxylic acid, which are separated by conventional means.

PREPARATION 4

4A. Formula 4 Where X is 6-$OCH_3$, and Y is —$(CH_2)_2$—

6-Methoxy-indane-1-carboxylic acid, 6.0 g (31 mmol), a compound of Formula 3, was dissolved in 50 ml of methylene chloride and reacted at ambient temperature with 4.0 ml (46 mmol) of oxalyl chloride in the presence of one drop of DMF. After 2 hours, the reaction mixture was brought to reflux and maintained for 15 minutes. It was then concentrated under vacuum and stirred for about 30 minutes, yielding 6-methoxy-indane-1-carboxylic acid chloride, which was sufficiently pure to be used for the next step.

4B. Formula 4 Varying X and Y

By following the procedure of part A and substituting for 6-methoxy-1-indane carboxylic acid the following:
indane-1-carboxylic acid,
6-nitro-indane-1-carboxylic acid,
6-methoxy-1,2,3,4-tetrahydronaphthalene-1-carboxylic acid,
1,2,3,4-tetrahydronaphthalene-1-carboxylic acid,
4,6-dimethoxy-1,2,3,4-tetrahydronaphthalene-1-carboxylic acid,
4,5,6-trichloro-1,2,3,4-tetrahydronaphthalene-1-carboxylic acid,
1,2-benzo-6-chloro-cycloheptane-1-carboxylic acid, and
1,2-benzo-cycloheptane-1-carboxylic acid;
there are obtained the following respective compounds:
indane-1-carboxylic acid chloride,
6-nitro-indane-1-carboxylic acid chloride,
6-methoxy-1,2,3,4-tetrahydronaphthalene-1-carboxylic acid chloride,
1,2,3,4-tetrahydronaphthalene-1-carboxylic acid chloride,
4,6-dimethoxy-1,2,3,4-tetrahydronaphthalene-1-carboxylic acid chloride,
4,5,6-trichloro-1,2,3,4-tetrahydronaphthalene-1-carboxylic acid chloride,
1,2-benzo-6-chloro-cycloheptane-1-carboxylic acid chloride, and
1,2-benzo-cycloheptane-1-carboxylic acid chloride.

PREPARATION 5

5A. Formula 5 Where X is 6—OCH$_3$, and Y is —(CH$_2$-)$_2$—

A solution of 6.8 g (30 mmol) 6-methoxy-indane-1-carboxylic acid chloride was dissolved in 40 ml of methylene chloride and added dropwise to a stirred solution of 4.5 g (36 mmol) of the dimethylacetal of methylaminoacetaldehyde and 5 ml (36 mmol) of triethylamine (itself dissolved in 50 ml of methylene chloride). The mixture was stirred at ambient temperature overnight and then concentrated to a small volume. The residue was treated with ether and water, and the resulting organic layer washed with dilute sulfuric acid, water, saturated sodium carbonate and saturated sodium chloride. After drying over K$_2$CO$_3$ the ether solution was concentrated to yield 8 g of 1-[N-methyl-N-(2,2-dimethoxyethyl)aminocarbonyl]-6-methoxy-indane, a dimethylacetal of Formula 5, as an oil; [ir (film) 1630 cm$^{-1}$].

5B. Formula 5 Varying X and Y

By following the procedure of part A and substituting for 6-methoxy-1-indane carboxylic acid chloride the following:
indane-1-carboxylic acid chloride,
6-nitro-indane-1-carboxylic acid chloride,
6-methoxy-1,2,3,4-tetrahydronaphthalene-1-carboxylic acid chloride,
1,2,3,4-tetrahydronaphthalene-1-carboxylic acid chloride,
4,6-dimethoxy-1,2,3,4-tetrahydronaphthalene-1-carboxylic acid chloride,
4,5,6-trichloro-1,2,3,4-tetrahydronaphthalene-1-carboxylic acid chloride,
1,2-benzo-6-chloro-cycloheptane-1-carboxylic acid chloride, and
1,2-benzo-cycloheptane-1-carboxylic acid chloride;
there are obtained the following respective compounds:
1-[N-methyl-N-(2,2-dimethoxyethyl)aminocarbonyl]indane,
1-[N-methyl-N-(2,2-dimethoxyethyl)aminocarbonyl]-6-nitro-indane,
1-[N-methyl-N-(2,2-dimethoxyethyl)aminocarbonyl]-6-methoxy-1,2,3,4-tetrahydronaphthalene,
1-[N-methyl-N-(2,2-dimethoxyethyl)aminocarbonyl]-1,2,3,4-tetrahydronaphthalene,
1-[N-methyl-N-(2,2-dimethoxyethyl)aminocarbonyl]-4,6-dimethoxy-1,2,3,4-tetrahydronaphthalene,
1-[N-methyl-N-(2,2-dimethoxyethyl)aminocarbonyl]-4,5,6-trichloro-1,2,3,4-tetrahydronaphthalene,
1-[N-methyl-N-(2,2-dimethoxyethyl)aminocarbonyl]-1,2-benzo-6-chloro-cycloheptane, and
1-[N-methyl-N-(2,2-dimethoxyethyl)aminocarbonyl]-1,2-benzo-cycloheptane.

PREPARATION 6

6A. Formula 6 Where X is 6—OCH$_3$, and Y is —(CH$_2$-)$_2$—

1-[N-methyl-N-(2,2-dimethoxyethyl)aminocarbonyl]-6-methoxy-indane 3.5 g (12 mmol), an amidoacetal compound of Formula 5, was dissolved in 20 ml of ether and added to 1.0 g (26 mmol) of LAH in 100 ml of ether. The reaction mixture was stirred at ambient temperature for 48 hours and then treated dropwise with 1 ml of water, 1 ml of 15% NaOH, and finally 3 ml of water. The insoluble inorganic materials were removed by filtration and the filtrate was concentrated to give the 3.1 g of 1-[N-methyl-N-(2,2-dimethoxyethyl)aminomethyl]-6-methoxy-indane, an aminoacetal of Formula 6, which is used without further purification.

6B. Formula 6 Varying X and Y

By following the procedure of part A and substituting for 1-[N-methyl-N-(2,2-dimethoxyethyl)aminocarbonyl]-6-methoxy-indane the following:
1-[N-methyl-N-(2,2-dimethoxyethyl)aminocarbonyl]indane,
1-[N-methyl-N-(2,2-dimethoxyethyl)aminocarbonyl]-6-nitro-indane,
1-[N-methyl-N-(2,2-dimethoxyethyl)aminocarbonyl]-6-methoxy-1,2,3,4-tetrahydronaphthalene,
1-[N-methyl-N-(2,2-dimethoxyethyl)aminocarbonyl]-1,2,3,4-tetrahydronaphthalene,
1-[N-methyl-N-(2,2-dimethoxyethyl)aminocarbonyl]-4,6-dimethoxy-1,2,3,4-tetrahydronaphthalene,
1-[N-methyl-N-(2,2-dimethoxyethyl)aminocarbonyl]-4,5,6-trichloro-1,2,3,4-tetrahydronaphthalene,
1-[N-methyl-N-(2,2-dimethoxyethyl)aminocarbonyl]-1,2-benzo-6-chloro-cycloheptane, and
1-[N-methyl-N-(2,2-dimethoxyethyl)aminocarbonyl]-1,2-benzo-cycloheptane;
there are obtained the following respective compounds:
1-[N-methyl-N-(2,2-dimethoxyethyl)aminomethyl]indane,
1-[N-methyl-N-(2,2-dimethoxyethyl)aminomethyl]-6-nitro-indane,
1-[N-methyl-N-(2,2-dimethoxyethyl)aminomethyl]-6-methoxy-1,2,3,4-tetrahydronaphthalene,
1-[N-methyl-N-(2,2-dimethoxyethyl)aminomethyl]-1,2,3,4-tetrahydronaphthalene,
1-[N-methyl-N-(2,2-dimethoxyethyl)aminomethyl]-4,6-dimethoxy-1,2,3,4-tetrahydronaphthalene, 1-[N-methyl-N-(2,2-dimethoxyethyl)aminomethyl]-4,5,6-trichloro-1,2,3,4-tetrahydronaphthalene,
1-[N-methyl-N-(2,2-dimethoxyethyl)aminomethyl]-1,2-benzo-6-chloro-cycloheptane, and
1-[N-methyl-N-(2,2-dimethoxyethyl)aminomethyl]-1,2-benzo-cycloheptane.

PREPARATION 7

7A. Formula 7 Where X is 5—OCH$_3$, and Y is —(CH$_2$)$_2$—

A mixture of 2.5 g (9 mmol) of 1-[N-methyl-N-(2,2-dimethoxyethyl)aminomethyl]-6-methoxy-indane, an aminoacetal of Formula 6, and about 3 ml of methylene chloride was stirred in an ice-water bath. Through a syringe, a total of 5 ml of trifluoromethane sulfuric acid was introduced in five portions, with stirring, which continued for 2 hours at 0° C. and then for 16 hours at ambient temperature. The reaction was then quenched by pouring the reaction mixture over crushed ice. Extraction of the resulting acid solution with ether served to remove neutral materials. The remaining acid solution was made alkaline with NaOH, and 1.3 g of 2-methyl-5-methoxy-1,8,9,9a-tetrahydro-2H-indeno[1,7-cd]azepine, an intermediate of Formula 7, was extracted with ether, as an oil.

7B. Formula 7 Varying X and Y

By following the procedure of part A and substituting for 1-[N-methyl-N-(2,2-dimethoxyethyl)aminomethyl]-6-methoxy-indane the following:
1-[N-methyl-N-(2,2-dimethoxyethyl)aminomethyl]indane,
1-[N-methyl-N-(2,2-dimethoxyethyl)aminomethyl]-6-nitro-indane,
1-[N-methyl-N-(2,2-dimethoxyethyl)aminomethyl]-6-methoxy-1,2,3,4-tetrahydronaphthalene,
1-[N-methyl-N-(2,2-dimethoxyethyl)aminomethyl]-1,2,3,4-tetrahydronaphthalene,
1-[N-methyl-N-(2,2-dimethoxyethyl)aminomethyl]-4,6-dimethoxy-1,2,3,4-tetrahydronaphthalene,
1-[N-methyl-N-(2,2-dimethoxyethyl)aminomethyl]-4,5,6-trichloro-1,2,3,4-tetrahydronaphthalene,
1-[N-methyl-N-(2,2-dimethoxyethyl)aminomethyl]-1,2-benzo-6-chloro-cycloheptane, and
1-[N-methyl-N-(2,2-dimethoxyethyl)aminomethyl]-1,2-benzo-cycloheptane;
there are obtained the following respective compounds:
2-methyl-1,8,9,9a-tetrahydro-2H-indeno[1,7-cd]azepine,
2-methyl-5-nitro-1,8,9,9a-tetrahydro-2H-indeno[1,7-cd]azepine,
2-methyl-5-methoxy-1,2,8,9,10,10a-hexahydronaphth[1,8-cd]azepine,
2-methyl-1,2,8,9,10,10a-hexahydronaphth[1,8-cd]azepine,
2-methyl-5,7-dimethoxy-1,2,8,9,10,10a-hexahydronaphth[1,8-cd]azepine,
2-methyl-5,6,7-trichloro-1,2,8,9,10,10a-hexahydronaphth[1,8-cd]azepine,
2-methyl-5-chloro-1,8,9,10,11,11a-hexahydro-2H-cyclohepta[c,d][3]benzazepine, and
2-methyl-1,8,9,10,11,11a-hexahydro-2H-cyclohepta[c,d][3]benzazepine.

PREPARATION 8

8A. Formula 8 Where X is Hydrogen, and Y is —(CH$_2$)$_3$—

A solution of 0.7 g (6.6 mmol) of cyanogen bromide in 25 ml of toluene is run into a 50° C. warm solution of 1.23 g (6.13 mmol) of 2-methyl-1,2,3,4,8,9,10,10a-octahydronaphth[1,8-cd]azepine in 30 ml of toluene. After 1 hour, the reaction mixture is concentrated to dryness. The solid that remains is dissolved in a small volume of methylene chloride and filtered through a small amount of silica gel to yield, after evaporation, 1.12 g of 2-cyano-1,2,3,4,8,9,10,10a-octahydronaphth[1,8-cd]azepine, an intermediate of Formula 8, as an off-white solid, mp 58°–60° C.

8B. Formula 8 Varying X and Y

By following the procedure of part A above and substituting for 2-methyl-1,2,3,4,8,9,10,10a-octahydronaphth[1,8-cd]azepine the following:
2-methyl-5-methoxy-1,3,4,8,9,9a-hexahydro-2H-indeno[1,7-cd]azepine,
2-methyl-1,3,4,8,9,9a-hexahydro-2H-indeno[1,7-cd]azepine,
2-methyl-5-nitro-1,3,4,8,9,9a-hexahydro-2H-indeno[1,7-cd]azepine,
2-methyl-5-methoxy-1,2,3,4,8,9,10,10a-octahydronaphth[1,8-cd]azepine,
2-methyl-5,7-dimethoxy-1,2,3,4,8,9,10,10a-octahydronaphth[1,8-cd]azepine,
2-methyl-5,6,7-trichloro-1,2,3,4,8,9,10,10a-octahydronaphth[1,8-cd]azepine,
2-methyl-5-chloro-1,3,4,8,9,10,11,11a-octahydro-2H-cyclohepta[c,d][3]benzazepine, and
2-methyl-1,3,4,8,9,10,11,11a-octahydro-2H-cyclohepta[c,d][3]benzazepine;
there are obtained the following respective compounds:
2-cyano-5-methoxy-1,3,4,8,9,9a-hexahydro-2H-indeno[1,7-cd]azepine,
2-cyano-1,3,4,8,9,9a-hexahydro-2H-indeno[1,7-cd]azepine,
2-cyano-5-nitro-1,3,4,8,9,9a-hexahydro-2H-indeno[1,7-cd]azepine,
2-cyano-5-methoxy-1,2,3,4,8,9,10,10a-octahydronaphth[1,8-cd]azepine,
2-cyano-5,7-dimethoxy-1,2,3,4,8,9,10,10a-octahydronaphth[1,8-cd]azepine,
2-cyano-5,6,7-trichloro-1,2,3,4,8,9,10,10a-octahydronaphth[1,8-cd]azepine,
2-cyano-5-chloro-1,3,4,8,9,10,11,11a-octahydro-2H-cyclohepta[c,d][3]benzazepine, and
2-cyano-1,3,4,8,9,10,11,11a-octahydro-2H-cyclohepta[c,d][3]benzazepine.

PREPARATION 9

9A. Formula 9 Where X is 5-OMe, and Y is —(CH$_2$)$_2$—

8.0 G (30.6 mmol), of 1-[N-methyl-N-(2,2-dimethoxyethyl)aminocarbonyl]-6-methoxy-indane, an amidoacetal compound of Formula 5 prepared, for example, as described in Preparation 5, is dissolved in 80.0 ml of acetic acid and treated with 8.0 ml of concentrated HCl for 6 hours at 80° C. The reaction mixture was quenched by pouring it over ice and then extracted with ether. The ether extract was stirred and saturated sodium bicarbonate was added until the aqueous phase remained alkaline. The ether layer was dried, filtered and concentrated to yield 600 mg of 1-oxo-2-methyl-5-methoxy-1,8,9,9a-tetrahydro-2H-indeno[1,7-cd]azepine, a lactam of Formula 9, which is used without further purification.

9B. Formula 9 Varying X and Y

By following the procedure of part A above and substituting for 1-[N-methyl-N-(2,2-dimethoxyethyl)aminocarbonyl]-6-methoxy-indane the following:

1-[N-methyl-N-(2,2-dimethoxyethyl)aminocarbonyl]indane,
1-[N-methyl-N-(2,2-dimethoxyethyl)aminocarbonyl]-6-nitro-indane,
1-[N-methyl-N-(2,2-dimethoxyethyl)aminocarbonyl]-6-methoxy-1,2,3,4-tetrahydronaphthalene,
1-[N-methyl-N-(2,2-dimethoxyethyl)aminocarbonyl]-1,2,3,4-tetrahydronaphthalene,
1-[N-methyl-N-(2,2-dimethoxyethyl)aminocarbonyl]-4,6-dimethoxy-1,2,3,4-tetrahydronaphthalene,
1-[N-methyl-N-(2,2-dimethoxyethyl)aminocarbonyl]-4,5,6-trichloro-1,2,3,4-tetrahydronaphthalene,
1-[N-methyl-N-(2,2-dimethoxyethyl)aminocarbonyl]-1,2-benzo-6-chloro-cycloheptane, and
1-[N-methyl-N-(2,2-dimethoxyethyl)aminocarbonyl]-1,2-benzo-cycloheptane;
there are obtained the following respective compounds:
1-oxo-2-methyl-1,8,9,9a-tetrahydro-2H-indeno[1,7-cd]azepine,
1-oxo-2-methyl-5-nitro-1,8,9,9a-tetrahydro-2H-indeno[1,7-cd]azepine,
1-oxo-2-methyl-5-methoxy-1,2,8,9,10,10a-hexahydronaphth[1,8-cd]azepine,
1-oxo-2-methyl-1,2,8,9,10,10a-hexahydronaphth[1,8-cd]azepine,
1-oxo-2-methyl-5,7-dimethoxy-1,2,8,9,10,10a-hexahydronaphth[1,8-cd]azepine,
1-oxo-2-methyl-5,6,7-trichloro-1,2,8,9,10,10a-hexahydronaphth[1,8-cd]azepine,
1-oxo-2-methyl-5-chloro-1,8,9,10,11,11a-hexahydro-2H-cyclohepta[c,d][3]benzazepine, and
1-oxo-2-methyl-1,8,9,10,11,11a-hexahydro-2H-cyclohepta[c,d][3]benzazepine.

PREPARATION 10

10A. Formula 10 Where X is 5-OMe, and Y is —(CH$_2$)$_2$—

1-Oxo-2-methyl-5-methoxy-1,8,9,9a-tetrahydro-2H-indeno[1,7-cd]azepine, a lactam of Formula 9, 600 mg (0.3 mmol), prepared, for example, as described in Preparation 9, is dissolved in 40 ml of ethanol and subjected to catalytic hydrogenation over 250 mg of 5% Pt/C for 24 hours at ambient temperature and atmospheric pressure. The catalyst is removed by filtration and the filtrate concentrated to yield 580 mg of a pure lactam intermediate compound of Formula 10, 1-oxo-2-methyl-5-methoxy-1,3,4,8,9,9a-hexahydro-2H-indeno[1,7-cd]azepine, (mp 141°-143° C.; ir 1630 cm$^{-1}$).

10B. Formula 10 Varying X and Y

By following the procedure of part A above and substituting for 1-oxo-2-methyl-5-methoxy-1,8,9,9a-tetrahydro-2H-indeno[1,7-cd]azepine the following:
1-oxo-2-methyl-1,8,9,9a-tetrahydro-2H-indeno[1,7-cd]azepine,
1-oxo-2-methyl-5-nitro-1,8,9,9a-tetrahydro-2H-indeno[1,7-cd]azepine,
1-oxo-2-methyl-5-methoxy-1,2,8,9,10,10a-hexahydronaphth[1,8-cd]azepine,
1-oxo-2-methyl-1,2,8,9,10,10a-hexahydronaphth[1,8-cd]azepine,
1-oxo-2-methyl-5,7-dimethoxy-1,2,8,9,10,10a-hexahydronaphth[1,8-cd]azepine,
1-oxo-2-methyl-5,6,7-trichloro-1,2,8,9,10,10a-hexahydronaphth[1,8-cd]azepine,
1-oxo-2-methyl-5-chloro-1,8,9,10,11,11a-hexahydro-2H-cyclohepta[c,d][3]benzazepine, and
1-oxo-2-methyl-1,8,9,10,11,11a-hexahydro-2H-cyclohepta[c,d][3]benzazepine;
there are obtained the following respective compounds:
1-oxo-2-methyl-1,3,4,8,9,9a-hexahydro-2H-indeno[1,7-cd]azepine,
1-oxo-2-methyl-5-nitro-1,3,4,8,9,9a-hexahydro-2H-indeno[1,7-cd]azepine,
1-oxo-2-methyl-5-methoxy-1,2,3,4,8,9,10,10a-octahydronaphth[1,8-cd]azepine,
1-oxo-2-methyl-1,2,3,4,8,9,10,10a-octahydronaphth[1,8-cd]azepine,
1-oxo-2-methyl-5,7-dimethoxy-1,2,3,4,8,9,10,10a-octahydronaphth[1,8-cd]azepine,
1-oxo-2-methyl-5,6,7-trichloro-1,2,3,4,8,9,10,10a-octahydronaphth[1,8-cd]azepine,
1-oxo-2-methyl-5-chloro-1,3,4,8,9,10,11,11a-octahydro-2H-cyclohepta[c,d][3]benzazepine, and
1-oxo-2-methyl-1,3,4,8,9,10,11,11a-octahydro-2H-cyclohepta[c,d][3]benzazepine.

PREPARATION 11

11A. Formula 11 where X is H, and Y is —(CH$_2$)$_3$—

A solution of 25.9 g (132.9 mmol) of 1,2,3,4-tetrahydronaphthylene-1-carboxylic acid chloride, an acid chloride of Formula 4 prepared, for example, as described in Preparation 4, was dissolved in 50 ml of methylene chloride, and added dropwise to a stirred solution of 29.9 g (398.7 mmol) of 2-(methylamino)ethanol in 100 ml of methylene chloride at 0° C. The mixture was stirred at ambient temperature for 10 minutes. 100 Ml of water was added and the organic layer was washed with dilute HCl, water, saturated NaHCO$_3$ and saturated NaCl. After drying over Na$_2$SO$_4$, the methylene chloride was concentrated to yield 30.65 g of 1-[N-(2-hydroxyethyl)-N-methylaminocarbonyl]-1,2,3,4-tetrahydronaphthalene, an amide intermediate of Formula 11, as an oil.

11B. Formula 11 Varying X and Y

By following the procedure of part A and substituting for 1,2,3,4-tetrahydronaphthalene-1-carboxylic acid chloride the following:
6-methoxy-indane-1-carboxylic acid chloride,
indane-1-carboxylic acid chloride,
6-nitro-indane-1-carboxylic acid chloride,
6-methoxy-1,2,3,4-tetrahydronaphthalene-1-carboxylic acid chloride,
4,6-dimethoxy-1,2,3,4-tetrahydronaphthalene-1-carboxylic acid chloride,
4,5,6-trichloro-1,2,3,4-tetrahydronaphthalene-1-carboxylic acid chloride,
1,2-benzo-6-chloro-cycloheptane-1-carboxylic acid chloride, and
1,2-benzo-cycloheptane-1-carboxylic acid chloride;
there are obtained the following respective compounds:
1-[N-(2-hydroxyethyl)-N-methylaminocarbonyl]-6-methoxy-indane,
1-[N-(2-hydroxyethyl)-N-methylaminocarbonyl]-indane,
1-[N-(2-hydroxyethyl)-N-methylaminocarbonyl]-6-nitro-indane,
1-[N-(2-hydroxyethyl)-N-methylaminocarbonyl]-6-methoxy-1,2,3,4-tetrahydronaphthalene,
1-[N-(2-hydroxyethyl)-N-methylaminocarbonyl]-4,6-dimethoxy-1,2,3,4-tetrahydronaphthalene,
1-[N-(2-hydroxyethyl)-N-methylaminocarbonyl]-4,5,6-trichloro-1,2,3,4-tetrahydronaphthalene,
1-[N-(2-hydroxyethyl)-N-methylaminocarbonyl]-1,2-benzo-6-chloro-cycloheptane, and
1-[N-(2-hydroxyethyl)-N-methylaminocarbonyl]-1,2-benzo-cycloheptane.

PREPARATION 12

12A. Formula 12 Where X is H, and Y is —(CH$_2$)$_3$—

To an incomplete solution of 7.5 g (200 mmol) of LAH in 200 ml of THF was added a solution of 30.65 g (131.4 mmol) of 1-[N-(2-hydroxyethyl)-N-methylaminocarbonyl]-1,2,3,4-tetrahydronaphthalene, a compound of Formula 11 prepared, for example, as described in Preparation 11, dissolved in 100 ml of THF. The reaction was stirred at reflux for 30 minutes, cooled to ambient temperature, and treated with 7.5 ml of water, 7.5 ml of 15% NaOH, and finally with 22.5 ml of water. Insoluble inorganic materials were removed by filtration and the filtrate concentrated to give 27.31 g of 1-[N-(2-hydroxyethyl)-N-methylaminomethyl]-1,2,3,4-tetrahydronaphthalene, an intermediate of Formula 12, as an oil.

12B. Formula 12 Varying X and Y

By following the procedure of part A and substituting for 1-[N-(2-hydroxyethyl)-N-methylaminocarbonyl]-1,2,3,4-tetrahydronaphthalene the following:

1-[N-(2-hydroxyethyl)-N-methylaminocarbonyl]-6-methoxy-indane,
1-[N-(2-hydroxyethyl)-N-methylaminocarbonyl]-indane,
1-[N-(2-hydroxyethyl)-N-methylaminocarbonyl]-6-nitro-indane,
1-[N-(2-hydroxyethyl)-N-methylaminocarbonyl]-6-methoxy-1,2,3,4-tetrahydronaphthalene,
1-[N-(2-hydroxyethyl)-N-methylaminocarbonyl]-4,6-dimethoxy-1,2,3,4-tetrahydronaphthalene,
1-[N-(2-hydroxyethyl)-N-methylaminocarbonyl]-4,5,6-trichloro-1,2,3,4-tetrahydronaphthalene,
1-[N-(2-hydroxyethyl)-N-methylaminocarbonyl]-1,2-benzo-6-chloro-cycloheptane, and
1-[N-(2-hydroxyethyl)-N-methylaminocarbonyl]-1,2-benzo-cycloheptane;

there are obtained the following respective compounds:

1-[N-(2-hydroxyethyl)-N-methylaminomethyl]-6-methoxy-indane,
1-[N-(2-hydroxyethyl)-N-methylaminomethyl]-indane,
1-[N-(2-hydroxyethyl)-N-methylaminomethyl]-6-nitro-indane,
1-[N-(2-hydroxyethyl)-N-methylaminomethyl]-6-methoxy-1,2,3,4-tetrahydronaphthalene,
1-[N-(2-hydroxyethyl)-N-methylaminomethyl]-4,6-dimethoxy-1,2,3,4-tetrahydronaphthalene,
1-[N-(2-hydroxyethyl)-N-methylaminomethyl]-4,5,6-trichloro-1,2,3,4-tetrahydronaphthalene,
1-[N-(2-hydroxyethyl)-N-methylaminomethyl]-1,2-benzo-6-chloro-cycloheptane, and
1-[N-(2-hydroxyethyl)-N-methylaminomethyl]-1,2-benzocycloheptane.

PREPARATION 13

13A. Formula 13 Where X is H, and Y is —(CH$_2$)$_2$—

A mixture of 150 ml of ethyl acetate and 50 ml of 40% aqueous methylamine (approx. 0.5M) was stirred in an ice bath, while a solution of 11.7 g (65 mmol) of indane-1-carboxylic acid chloride, a compound of Formula 4 prepared, for example, as described in Preparation 4, dissolved 40 ml of ethyl acetate was added over a period of 15 minutes. Stirring was continued at ambient temperature for an additional 4 hours. The organic layer is separated, washed three times with water, once with 10% HCl, and once with saturated sodium bicarbonate. Evaporation of the ethyl acetate yielded 9.0 g of 1-methylaminocarbonyl-indane, an amide of Formula 13; (mp 107°-109° C.; ir 1635 cm$^{-1}$).

13B. Formula 13 Varying X and Y

By following the procedure of part A and substituting for indane-1-carboxylic acid chloride the following:
6-methoxy-indane-1-carboxylic acid chloride,
6-nitro-indane-1-carboxylic acid chloride,
6-methoxy-1,2,3,4-tetrahydronaphthalene-1-carboxylic acid chloride,
1,2,3,4-tetrahydronaphthalene-1-carboxylic acid chloride,
4,6-dimethoxy-1,2,3,4-tetrahydronaphthalene-1-carboxylic acid chloride,
4,5,6-trichloro-1,2,3,4-tetrahydronaphthalene-1-carboxylic acid chloride,
1,2-benzo-6-chloro-cycloheptane-1-carboxylic acid chloride, and
1,2-benzo-cycloheptane-1-carboxylic acid chloride;
there are obtained the following respective compounds:
1-methylaminocarbonyl-6-methoxy-indane,
1-methylaminocarbonyl-6-nitro-indane,
1-methylaminocarbonyl-6-methoxy-1,2,3,4-tetrahydronaphthalene,
1-methylaminocarbonyl-1,2,3,4-tetrahydronaphthalene,
1-methylaminocarbonyl-4,6-dimethoxy-1,2,3,4-tetrahydronaphthalene,
1-methylaminocarbonyl-4,5,6-trichloro-1,2,3,4-tetrahydronaphthalene,
1-methylaminocarbonyl-1,2-benzo-6-chlorocycloheptane, and
1-methylaminocarbonyl-1,2-benzo-cycloheptane.

13C. Formula 13 Varying R

By following the procedure of part A and substituting another alkylamine, e.g., N-propylamine, for methylamine, there are obtained the corresponding alkylaminocarbonyl compounds of Formula 13, e.g., 1-propylaminocarbonyl-indane.

PREPARATION 14

14A. Formula 14 Where X is H, and Y is —(CH$_2$)$_2$—

A mixture of 4.0 g (0.1M) of LAH and 400 ml of ether was stirred while a solution of 9.0 g (51 mmol) of 1-methylaminocarbonyl-indane, a compound of Formula 13 prepared, for example, as described in Preparation 13, dissolved 200 ml of THF was added over a period of 30 minutes. The reaction mixture was stirred and heated to reflux for 6 hours, and then stirred at ambient temperature for an additional 16 hours. The reaction mixture was then digested by treating dropwise with water, 15% NaOH, and then water, yielding 1-methylaminomethyl-indane, an intermediate amine of Formula 14; (HCl salt, ethanol-ether, mp 169°-171° C.).

14B. Formula 14 Varying X and Y

By following the procedure of part A and substituting for 1-methylaminocarbonyl-indane the following:
1-methylaminocarbonyl-6-methoxy-indane,
1-methylaminocarbonyl-6-nitro-indane,
1-methylaminocarbonyl-6-methoxy-1,2,3,4-tetrahydronaphthalene,
1-methylaminocarbonyl-1,2,3,4-tetrahydronaphthalene,
1-methylaminocarbonyl-4,6-dimethoxy-1,2,3,4-tetrahydronaphthalene,
1-methylaminocarbonyl-4,5,6-trichloro-1,2,3,4-tetrahydronaphthalene,
1-methylaminocarbonyl-1,2-benzo-6-chlorocycloheptane, and
1-methylaminocarbonyl-1,2-benzo-cycloheptane; there are obtained the following respective compounds:

1-methylaminomethyl-6-methoxy-indane,
1-methylaminomethyl-6-nitro-indane,
1-methylaminomethyl-6-methoxy-1,2,3,4-tetrahydronaphthalene,
1-methylaminomethyl-1,2,3,4-tetrahydronaphthalene,
1-methylaminomethyl-4,6-dimethoxy-1,2,3,4-tetrahydronaphthalene,
1-methylaminomethyl-4,5,6-trichloro-1,2,3,4-tetrahydronaphthalene,
1-methylaminomethyl-1,2-benzo-6-chlorocycloheptane, and
1-methylaminomethyl-1,2-benzo-cycloheptane.

14C. Formula 14 Varying R

By following the procedure of part A and substituting another alkylaminocarbonyl compound of Formula 13, e.g., 1-propylaminocarbonyl-indane, for 1-methylaminocarbonyl-indane, there are obtained the corresponding alkylaminomethyl compounds, e.g., 1-propylaminomethyl-indane.

PREPARATION 15

15A. Formula 15 Where X is H, and Y is —(CH$_2$)$_2$—

A mixture of 50 ml of water containing 13 g of potassium carbonate, 100 ml of ethyl acetate and 3.8 g (24 mmol) of 1-methylaminomethyl-indane, a compound of Formula 14 prepared, for example, as described in Preparation 14, was stirred over an ice bath and a solution of 3.0 g (27 mmol) of chloroacetylchloride dissolved in 25 ml of ethyl acetate was added over a period of 1 hour. Stirring was continued for an additional 30 minutes at ambient temperature. The ethyl acetate layer was separated and concentrated to yield 5.1 g of 1-(N-chloroacetyl-N-methyl)aminomethyl-indane, a chloroacetamide of Formula 15, as an oil.

15B. Formula 15 Varying X and Y

By following the procedure of part A and substituting for 1-methylaminomethyl-indane the following:
1-methylaminomethyl-6-methoxy-indane,
1-methylaminomethyl-6-nitro-indane,
1-methylaminomethyl-6-methoxy-1,2,3,4-tetrahydronaphthalene,
1-methylaminomethyl-1,2,3,4-tetrahydronaphthalene,
1-methylaminomethyl-4,6-dimethoxy-1,2,3,4-tetrahydronaphthalene,
1-methylaminomethyl-4,5,6-trichloro-1,2,3,4-tetrahydronaphthalene,
1-methylaminomethyl-1,2-benzo-6-chlorocycloheptane, and
1-methylaminomethyl-1,2-benzo-cycloheptane;
there are obtained the following respective compounds:
1-(N-chloroacetyl-N-methyl)aminomethyl-6-methoxy-indane,
1-(N-chloroacetyl-N-methyl)aminomethyl-6-nitro-indane,
1-(N-chloroacetyl-N-methyl)aminomethyl-6-methoxy-1,2,3,4-tetrahydronaphthalene,
1-(N-chloroacetyl-N-methyl)aminomethyl-1,2,3,4-tetrahydronaphthalene,
1-(N-chloroacetyl-N-methyl)aminomethyl-4,6-dimethoxy-1,2,3,4-tetrahydronaphthalene,
1-(N-chloroacetyl-N-methyl)aminomethyl-4,5,6-trichloro-1,2,3,4-tetrahydronaphthalene,
1-(N-chloroacetyl-N-methyl)aminomethyl-1,2-benzo-6-chloro-cycloheptane, and
1-(N-chloroacetyl-N-methyl)aminomethyl-1,2-benzo-cycloheptane.

15C. Formula 15 Varying R

By following the procedure of part A and substituting another alkylaminomethyl compound of Formula 14, e.g., 1-propylaminomethyl-indane, for 1-methylaminomethyl-indane, there are obtained the corresponding 1-(N-chloroacetyl-N-alkyl)aminomethyl compounds, e.g., 1-(N-chloroacetyl-N-propyl)aminomethyl-indane.

PREPARATION 16

16A. Formula 16 Where X is H, and Y is —(CH$_2$)$_2$—

A sample of 950 mg (4 mmol) of 1-(N-chloroacetyl-N-methyl)aminomethyl-indane, a chloroacetamide compound of Formula 15 prepared, for example, as described in Preparation 15, was introduced via syringe to a 140° C. hot, stirred mixture of 1.9 g (14 mmol) of aluminum chloride in 5 ml of trichlorobenzene. After 2 hours, the reaction was quenched by pouring over a mixture of ice and 10% HCl. Organic products and trichlorobenzene were extracted out with ethyl acetate. The extract was chromatographed (silica gel; 40% ethyl acetate in hexane) to separate 250 mg of 2-methyl-3-oxo-1,3,4,8,9,9a-hexahydro-2H-indeno[1,7-cd]azepine (mp 62°–68° C.), a lactam product of Formula 16 from side-products and from trichlorobenzene. Recrystallization from cyclohexane furnished analytically pure product; (mp 67°–70° C.; ms 201 (M+); ir, KBr salt 1650, 1640 cm$^{-1}$).

16B. Formula 16 Varying X and Y

By following the procedure of part A and substituting for 1-(N-chloroacetyl-N-methyl)aminomethyl-indane the following:
1-(N-chloroacetyl-N-methyl)aminomethyl-6-methoxy-indane,
1-(N-chloroacetyl-N-methyl)aminomethyl-6-nitro-indane,
1-(N-chloroacetyl-N-methyl)aminomethyl-6-methoxy-1,2,3,4-tetrahydronaphthalene,
1-(N-chloroacetyl-N-methyl)aminomethyl-1,2,3,4-tetrahydronaphthalene,
1-(N-chloroacetyl-N-methyl)aminomethyl-4,6-dimethoxy-1,2,3,4-tetrahydronaphthalene,
1-(N-chloroacetyl-N-methyl)aminomethyl-4,5,6-trichloro-1,2,3,4-tetrahydronaphthalene,
1-(N-chloroacetyl-N-methyl)aminomethyl-1,2-benzo-6-chloro-cycloheptane, and
1-(N-chloroacetyl-N-methyl)aminomethyl-1,2-benzo-cycloheptane;
there are obtained the following respective compounds:
2-methyl-3-oxo-5-methoxy-1,3,4,8,9,9a-hexahydro-2H-indeno[1,7-cd]azepine,
2-methyl-3-oxo-5-nitro-1,3,4,8,9,9a-hexahydro-2H-indeno[1,7-cd]azepine,
2-methyl-3-oxo-5-methoxy-1,2,3,4,8,9,10,10a-octahydronaphth[1,8-cd]azepine,
2-methyl-3-oxo-1,2,3,4,8,9,10,10a-octahydronaphth[1,8-cd]azepine,
2-methyl-3-oxo-5,7-dimethoxy-1,2,3,4,8,9,10,10a-octahydronaphth[1,8-cd]azepine,
2-methyl-3-oxo-5,6,7-trichloro-1,2,3,4,8,9,10,10a-octahydronaphth[1,8-cd]azepine,
2-methyl-3-oxo-5-chloro-1,3,4,8,9,10,11,11a-octahydro-2H-cyclohepta[c,d][3]benzazepine, and
2-methyl-3-oxo-1,3,4,8,9,10,11,11a-octahydro-2H-cyclohepta[c,d][3]benzazepine.

16C. Formula 16 Varying R

By following the procedure of part A and substituting another 1-(N-chloroacetyl-N-alkyl)aminomethyl compound, e.g., 1-(N-chloroacetyl-N-propyl- )aminomethyl-indane for 1-(N-chloroacetyl-N-methyl-)aminomethyl-indane, there are obtained the corresponding N-alkyl-lactams, e.g., 2-propyl-3-oxo-1,3,4,8,9,9a-hexahydro-2H-indeno-[1,7-cd]azepine.

PREPARATION 17

17A. Formula 17 where Y is —(CH$_2$)$_2$—

A solution of 0.55 g (2.7 mmol) of 2-methyl-3-oxo-1,3,4,8,9,9a-hexahydro-2H-indeno[1,7-cd]azepine, a compound of Formula 16 prepared, for example, as described in Preparation 16, and 0.75 g (2.8 mmol) of ferric chloride hexahydrate in 20 ml of acetonitrile was stirred in an ice bath. Acetonitrile (5 ml) containing about 0.9 g of chlorine was added, and the reaction mixture was stirred for 30 minutes at 0° C., and an additional 30 minutes at ambient temperature. The reaction mixture was concentrated and the residual mixture treated with ether and water. The ether contained 640 mg of 2-methyl-3-oxo-5-chloro-1,3,4,8,9,9a-hexahydro-2H-indeno[1,7-cd]azepine, a chlorinated lactam of Formula 17.

17B. Formula 17 where Y is —(CH$_2$)$_3$— or —(CH$_2$)$_4$—

By following the procedure of part A and substituting lactams of Formula 16 where Y is —(CH$_2$)$_3$— or —(CH$_2$)$_4$— there are obtained mixtures of chlorinated products, which are separable by column chromatography to give the corresponding compounds of Formula 17.

17C. Formula 17 Varying R

By following the procedure of part A and substituting another N-alkyl-lactams, e.g., 2-propyl-3-oxo-1,3,4,8,9,9a-hexahydro-2H-indeno[1,7-cd]azepine, for 2-methyl-3-oxo-1,3,4,8,9,9a-hexahydro-2H-indeno[1,7-cd]azepine, there are obtained the corresponding chlorinated lactams of Formula 17, e.g., 2-propyl-3-oxo-5-chloro-1,3,4,8,9,9a-hexahydro-2H-indeno[1,7-cd]azepine.

EXAMPLE 1

2-Methyl-5-methoxy-1,3,4,8,9,10,11,11a-octahydro-2H-cyclohepta[c,d][3]benzazepine 1A. Formula I Where R is Methyl, R$^1$ and R$^2$ are Hydrogen, R$^3$ is OCH$_3$, and Y is —(CH$_2$)$_4$—

2-Methyl-5-methoxy-1,8,9,10,11,11a-hexahydro-2H-cyclohepta[c,d][3]benzazepine 1.3 g, prepared, e.g., as described in Preparation 7, was dissolved in an 40 ml of ethanol and 0.5 ml of concentrated HCl, and hydrogenated over 400 mg of 5% Pd/C for 1 hour at atmospheric pressure. The catalyst was removed by filtration and the filtrate concentrated, followed by the addition of aqueous NaOH to yield 2-methyl-6-methoxy-1,3,4,8,9,10,11,11a-octahydro-2H-cyclohepta-[c,d][3]benzazepine, a product compound of Formula I, as the free base. This product was extracted with ether, the removal of which left 600 mg of the product as an oil.

1B. Formula I where R is Methyl, Varying R$^1$, R$^2$, R$^3$ and Y

By following the procedure of part A and substituting for 2-methyl-5-methoxy-1,8,9,10,11,11a-hexahydro-2H-cyclohepta[c,d][3]benzazepine the following:
2-methyl-5-methoxy-1,8,9,9a-tetrahydro-2H-indeno[1,7-cd]azepine,
2-methyl-1,8,9,9a-tetrahydro-2H-indeno[1,7-cd]azepine,
2-methyl-5-nitro-1,8,9,9a-tetrahydro-2H-indeno[1,7-cd]azepine,
2-methyl-5-chloro-1,8,9,9a-tetrahydro-2H-indeno[1,7-cd]azepine,
2-methyl-5-methoxy-1,2,8,9,10,10a-hexahydronaphth[1,8-cd]azepine,
2-methyl-1,2,8,9,10,10a-hexahydronaphth[1,8-cd]azepine,
2-methyl-5-chloro-1,2,8,9,10,10a-hexahydronaphth[1,8-cd]azepine,
2-methyl-7-chloro-1,2,8,9,10,10a-hexahydronaphth[1,8-cd]azepine,
2-methyl-5,7-dimethoxy-1,2,8,9,10,10a-hexahydronaphth[1,8-cd]azepine,
2-methyl-5,6,7-trichloro-1,2,8,9,10,10a-hexahydronaphth[1,8-cd]azepine,
2-methyl-5-trifluoromethyl-1,8,9,10,11,11a-hexahydro-2H-cyclohepta[c,d][3]benzazepine,
2-methyl-7-methylthio-1,8,9,10,11,11a-hexahydro-2H-cyclohepta[c,d][3]benzazepine,
2-methyl-5-formamido-1,8,9,10,11,11a-hexahydro-2H-cyclohepta[c,d][3]benzazepine,
2-methyl-6-acetamido-1,8,9,10,11,11a-hexahydro-2H-cyclohepta[c,d][3]benzazepine,
2-methyl-5-chloro-1,8,9,10,11,11a-hexahydro-2H-cyclohepta[c,d][3]benzazepine,
2-methyl-7-chloro-1,8,9,10,11,11a-hexahydro-2H-cyclohepta[c,d][3]benzazepine, and
2-methyl-1,8,9,10,11,11a-hexahydro-2H-cyclohepta[c,d][3]benzazepine;
there are obtained the following respective compounds:
2-methyl-5-methoxy-1,3,4,8,9,9a-hexahydro-2H-indeno[1,7-cd]azepine (HBr salt, mp 250°–252° C.),
2-methyl-1;3,4,8,9,9a-hexahydro-2H-indeno[1,7-cd]azepine (HBr salt, mp 262°–263° C.),
2-methyl-5-nitro-1,3,4,8,9,9a-hexahydro-2H-indeno[1,7-cd]azepine,
2-methyl-5-chloro-1,3,4,8,9,9a-hexahydro-2H-indeno[1,7-cd]azepine (HBr salt, mp 279°–281° C.),
2-methyl-5-methoxy-1,2,3,4,8,9,10,10a-octahydronaphth[1,8-cd]azepine (HCl salt, mp 214°–215° C.),
2-methyl-1,2,3,4,8,9,10,10a-octahydronaphth[1,8-cd]azepine (HCl salt, mp 185°–186° C.),
2-methyl-5-chloro-1,2,3,4,8,9,10,10a-octahydronaphth[1,8-cd]azepine (HCl salt, mp 233°–234° C.),
2-methyl-7-chloro-1,2,3,4,8,9,10,10a-octahydronaphth[1,8-cd]azepine (HCl salt, mp 224°–226° C.),
2-methyl-5,7-dimethoxy-1,2,3,4,8,9,10,10a-octahydronaphth[1,8-cd]azepine,
2-methyl-5,6,7-trichloro-1,2,3,4,8,9,10,10a-octahydronaphth[1,8-cd]azepine,
2-methyl-5-trifluoromethyl-1,3,4,8,9,10,11,11a-octahydro-2H-cyclohepta[c,d][3]benzazepine,
2-methyl-7-methylthio-1,3,4,8,9,10,11,11a-octahydro-2H-cyclohepta[c,d][3]benzazepine,
2-methyl-5-formamido-1,3,4,8,9,10,11,11a-hexahydro-2H-cyclohepta[c,d][3]benzazepine,
2-methyl-6-acetamido-1,3,4,8,9,10,11,11a-hexahydro-2H-cyclohepta[c,d][3]benzazepine,
2-methyl-5-chloro-1,3,4,8,9,10,11,11a-octahydro-2H-cyclohepta[c,d][3]benzazepine (HBr salt, mp 191°–193° C.),
2-methyl-7-chloro-1,3,4,8,9,10,11,11a-octahydro-2H-cyclohepta[c,d][3]benzazepine (HBr salt, mp 209°–211° C.), and
2-methyl-1,3,4,8,9,10,11,11a-octahydro-2H-cyclohepta[c,d][3]benzazepine (HCl salt, mp 184°–186° C.).

EXAMPLE 2

1,2,3,4,8,9,10,10a-octahydronaphth[1,8-cd]azepine

2A. Formula I Where R, $R^1$, $R^2$, and $R^3$ are Hydrogen, and Y is —(CH$_2$)$_3$—

A solution of 1.3 g (6.1 mmol) of 2-cyano-1,2,3,4,8,9,10,10a-octahydronaphth[1,8-cd]azepine, an intermediate of Formula 8 prepared, for example, as described in Preparation 8A, in a mixture of 40 ml of acetic acid and 40 ml of 20% hydrochloric acid, was kept at reflux for 20 hours. The solution was concentrated to a small volume, approximately 30 ml of water was added and neutral materials were removed by extraction with ether. The aqueous layer was made basic by addition of NaOH, and the product was extracted with ether. After evaporation of the ether, 0.8 g of 1,2,3,4,8,9,10,10a-octahydronaphth[1,8-cd]azepine was obtained as an oil (HCl salt, mp 207°-209° C.).

2B. Formula I Where R is Hydrogen, Varying $R^1$, $R^2$, $R^3$ and Y

By following the procedure of part A above and substituting for 2-cyano-1,2,3,4,8,9,10,10a-octahydronaphth[1,8-cd]azepine the following:

2-cyano-5-methoxy-1,3,4,8,9,9a-hexahydro-2H-indeno[1,7-cd]azepine, 2-cyano-1,3,4,8,9,9a-hexahydro-2H-indeno[1,7-cd]azepine, 2-cyano-5-nitro-1,3,4,8,9,9a-hexahydro-2H-indeno[1,7-cd]azepine, 2-cyano-5-methoxy-1,2,3,4,8,9,10,10a-octahydronaphth[1,8-cd]azepine, 2-cyano-5,7-dimethoxy-1,2,3,4,8,9,10,10a-octahydronaphth[1,8-cd]azepine, 2-cyano-5,6,7-trichloro-1,2,3,4,8,9,10,10a-octahydronaphth[1,8-cd]azepine, 2-cyano-5-chloro-1,3,4,8,9,10,11,11a-octahydro-2H-cyclohepta[c,d][3]benzazepine, and 2-cyano-1,3,4,8,9,10,11,11a-octahydro-2H-cyclohepta[c,d][3]benzazepine;

there are obtained the following respective compounds:

5-methoxy-1,3,4,8,9,9a-hexahydro-2H-indeno[1,7-cd]azepine, 1,3,4,8,9,9a-hexahydro-2H-indeno[1,7-cd]azepine, 5-nitro-1,3,4,8,9,9a-hexahydro-2H-indeno[1,7-cd]azepine, 5-methoxy-1,2,3,4,8,9,10,10a-octahydronaphth[1,8-cd]azepine, 5,7-dimethoxy-1,2,3,4,8,9,10,10a-octahydronaphth[1,8-cd]azepine, 5,6,7-trichloro-1,2,3,4,8,9,10,10a-octahydronaphth[1,8-cd]azepine, 5-chloro-1,3,4,8,9,10,11,11a-octahydro-2H-cyclohepta[c,d][3]benzazepine, and 1,3,4,8,9,10,11,11a-octahydro-2H-cyclohepta[c,d][3]benzazepine.

EXAMPLE 3

2-(Prop-2-enyl)-1,2,3,4,8,9,10,10a-octahydronaphth[1,8-cd]azepine

3A. Formula I Where R is Alkenyl, $R^1$, $R^2$, and $R^3$ are Hydrogen, and Y is —(CH$_2$)$_3$—

1,2,3,4,8,9,10,10a-Octahydronaphth[1,8-cd]azepine, 0.5 g, a compound of Formula I prepared, e.g., as described in Example 2, is dissolved in 50 ml of ethanol and reacted with 0.2 g of 3-bromo-1-propene for 16 hours in the presence of 2 g of potassium carbonate, at room temperature. 2-(Prop-2-enyl)-1,2,3,4,8,9,10,10a-octahydronaphth[1,8-cd]azepine, a compound according to Formula I, is isolated and purified in the usual manner. (HCl salt, mp 158°-161° C.).

3B. Formula I Where R is Alkenyl, Varying $R^1$, $R^2$, $R^3$ and Y

By following the procedure of part A above and substituting for 1,2,3,4,8,9,10,10a-octahydronaphth[1,8-cd]azepine the following:

5-methoxy-1,3,4,8,9,9a-hexahydro-2H-indeno[1,7-cd]azepine, 1,3,4,8,9,9a-hexahydro-2H-indeno[1,7-cd]azepine, 5-nitro-1,3,4,8,9,9a-hexahydro-2H-indeno[1,7-cd]azepine, 5-methoxy-1,2,3,4,8,9,10,10a-octahydronaphth[1,8-cd]azepine, 5,7-dimethoxy-1,2,3,4,8,9,10,10a-octahydronaphth[1,8-cd]azepine, 5,6,7-trichloro-1,2,3,4,8,9,10,10a-octahydronaphth[1,8-cd]azepine, 5-chloro-1,3,4,8,9,10,11,11a-octahydro-2H-cyclohepta[c,d][3]benzazepine, and 1,3,4,8,9,10,11,11a-octahydro-2H-cyclohepta[c,d][3]benzazepine;

there are obtained the following respective compounds:

2-(prop-2-enyl)-5-methoxy-1,3,4,8,9,9a-hexahydro-2H-indeno[1,7-cd]azepine, 2-(prop-2-enyl)-1,3,4,8,9,9a-hexahydro-2H-indeno[1,7-cd]azepine, 2-(prop-2-enyl)-5-nitro-1,3,4,8,9,9a-hexahydro-2H-indeno[1,7-cd]azepine, 2-(prop-2-enyl)-5-methoxy-1,2,3,4,8,9,10,10a-octahydronaphth[1,8-cd]azepine, 2-(prop-2-enyl)-5,7-dimethoxy-1,2,3,4,8,9,10,10a-octahydronaphth[1,8-cd]azepine, 2-(prop-2-enyl)-5,6,7-trichloro-1,2,3,4,8,9,10,10a-octahydronaphth[1,8-cd]azepine, 2-(prop-2-enyl)-5-chloro-1,3,4,8,9,10,11,11a-octahydro-2H-cyclohepta[c,d][3]benzazepine, and 2-(prop-2-enyl)-1,3,4,8,9,10,11,11a-octahydro-2H-cyclohepta[c,d][3]benzazepine.

EXAMPLE 4

2-Methyl-5-methoxy-1,3,4,8,9,9a-hexahydro-2H-indeno[1,7-cd]azepine

4A. Formula I Where R is Methyl, $R^1$ and $R^2$ are Hydrogen, $R^3$ is Methoxy, and Y is —(CH$_2$)$_2$—

A sample of 550 mg (2.7 mmol) of 1-oxo-2-methyl-5-methoxy-1,3,4,8,9,9a-hexahydro-2H-indeno[1,7-cd]azepine, a compound of Formula 10 prepared, for example, as described in Preparation 10A, was dissolved in 100 ml of diethylether followed by the addition of 750 mg (19 mmol) of LAH. The reaction was allowed to proceed for 24 hours at ambient temperature. The reaction mixture is treated dropwise with about 1 ml of water, 1 ml of 15% NaOH, and then 3 ml of water. Insoluble inorganic materials are removed by filtration and the filtrate concentrated to give 2-methyl-5-methoxy-1,3,4,8,9,9a-hexahydro-2H-indeno[1,7-cd]azepine, a compound of Formula I, as the free base; (HBr salt, mp 250°-252° C.).

4B. Formula I Where R is Methyl, Varying $R^1$, $R^2$, $R^3$ and Y

By following the procedure of part A and substituting for 1-oxo-2-methyl-5-methoxy-1,3,4,8,9,9a-hexahydro-2H-indeno[1,7-cd]azepine the following:

1-oxo-2-methyl-1,3,4,8,9,9a-hexahydro-2H-indeno[1,7-cd]azepine, 1-oxo-2-methyl-5-nitro-1,3,4,8,9,9a-hexahydro-2H-indeno[1,7-cd]azepine,
1-oxo-2-methyl-5-chloro-1,3,4,8,9,9a-hexahydro-2H-indeno[1,7-cd]azepine,
1-oxo-2-methyl-5-methoxy-1,2,3,4,8,9,10,10a-octahydronaphth[1,8-cd]azepine,
1-oxo-2-methyl-1,2,3,4,8,9,10,10a-octahydronaphth[1,8-cd]azepine,
1-oxo-2-methyl-5-chloro-1,2,3,4,8,9,10,10a-octahydronaphth[1,8-cd]azepine,
1-oxo-2-methyl-7-chloro-1,2,3,4,8,9,10,10a-octahydronaphth[1,8-cd]azepine,
1-oxo-2-methyl-5,7-dimethoxy-1,2,3,4,8,9,10,10a-octahydronaphth[1,8-cd]azepine,
1-oxo-2-methyl-5,6,7-trichloro-1,2,3,4,8,9,10,10a-octahydronaphth[1,8-cd]azepine,
1-oxo-2-methyl-5-chloro-1,3,4,8,9,10,11,11a-octahydro-2H-cyclohepta[c,d][3]benzazepine,
1-oxo-2-methyl-7-chloro-1,3,4,8,9,10,11,11a-octahydro-2H-cyclohepta[c,d][3]benzazepine, and
1-oxo-2-methyl-1,3,4,8,9,10,11,11a-octahydro-2H-cyclohepta[c,d][3]benzazepine;
there are obtained the following respective compounds:
2-methyl-1,3,4,8,9,9a-hexahydro-2H-indeno[1,7-cd]azepine (HBr salt, mp 262°–263° C.),
2-methyl-5-nitro-1,3,4,8,9,9a-hexahydro-2H-indeno[1,7-cd]azepine,
2-methyl-5-chloro-1,3,4,8,9,9a-hexahydro-2H-indeno[1,7-cd]azepine (HBr salt, mp 262°–263° C.),
2-methyl-5-methoxy-1,2,3,4,8,9,10,10a-octahydronaphth[1,8-cd]azepine (HCl salt, mp 214°–215° C.),
2-methyl-1,2,3,4,8,9,10,10a-octahydronaphth[1,8-cd]azepine (HCl salt, mp 185°–186° C.),
2-methyl-5-chloro-1,2,3,4,8,9,10,10a-octahydronaphth[1,8-cd]azepine (HCl salt, mp 233°–234° C.),
2-methyl-7-chloro-1,2,3,4,8,9,10,10a-octahydronaphth[1,8-cd]azepine (HCl salt, mp 224°–226° C.),
2-methyl-5,7-dimethoxy-1,2,3,4,8,9,10,10a-octahydronaphth[1,8-cd]azepine,
2-methyl-5,6,7-trichloro-1,2,3,4,8,9,10,10a-octahydronaphth[1,8-cd]azepine,
2-methyl-5-chloro-1,3,4,8,9,10,11,11a-octahydro-2H-cyclohepta[c,d][3]benzazepine (HBr salt, mp 191°–193° C.),
2-methyl-7-chloro-1,3,4,8,9,10,11,11a-octahydro-2H-cyclohepta[c,d][3]benzazepine (HBr salt, mp 209°–211° C.), and
2-methyl-1,3,4,8,9,10,11,11a-octahydro-2H-cyclohepta[c,d][3]benzazepine (HCl salt, mp 184°–186° C.).

EXAMPLE 5

2-Methyl-1,2,3,4,8,9,10,10a-octahydronaphth[1,8-cd]azepine

5A. Formula I Where R is Methyl, $R^1$, $R^2$, and $R^3$ are Hydrogen, and Y is —(CH$_2$)$_3$—

To a stirred solution of 27.0 g (0.126M) of 1-[N-(2-hydroxyethyl)-N-methylaminomethyl]-1,2,3,4-tetrahydronaphthalene, a compound of Formula 12 prepared, for example, as described in Preparation 12, dissolved in 170 ml of trichlorobenzene, at ambient temperature, was added 10.0 g (0.048M) of phosphorous pentachloride. The mixture was then heated to 110° C., and 34.0 g (0.255M) of aluminum chloride was added in portions over a period of 30 minutes. The temperature was increased 200° C. and the mixture stirred for an additional 3 hours. The reaction mixture was allowed to cool 80° C., and was then carefully combined with 900 ml of approximately 12% HCl. Toluene was added and the organic layers were removed in a separatory funnel. The remaining aqueous phase was made alkaline by the addition of 50% NaOH, and the product was extracted with ethyl acetate. The ethylacetate was evaporated and the remaining crude product purified, first by column chromatography (silica gel; 5% methanol in ethyl acetate) and finally by distillation; to yield 2-methyl-1,2,3,4,8,9,10,10a-octahydronaphth[1,8-cd]azepine (bp 105°–110° C. at 0.1 mm); (HCl salt, from ethanol-hydrogen chloride, mp 185°–186° C.).

5B. Formula I Where R is Methyl, Varying $R^1$, $R^2$, $R^3$, and Y

By following the procedure of part A and substituting for 1-[N-(2-hydroxyethyl)-N-methylaminomethyl]-1,2,3,4-tetrahydronaphthalene the following:
1-[N-(2-hydroxyethyl)-N-methylaminomethyl]-6-methoxy-indane,
1-[N-(2-hydroxyethyl)-N-methylaminomethyl]-indane,
1-[N-(2-hydroxyethyl)-N-methylaminomethyl]-6-nitro-indane,
1-[N-(2-hydroxyethyl)-N-methylaminomethyl]-6-chloro-indane,
1-[N-(2-hydroxyethyl)-N-methylaminomethyl]-6-methoxy-1,2,3,4-tetrahydronaphthalene,
1-[N-(2-hydroxyethyl)-N-methylaminomethyl]-6-chloro-1,2,3,4-tetrahydronaphthalene,
1-[N-(2-hydroxyethyl)-N-methylaminomethyl]-4-chloro-1,2,3,4-tetrahydronaphthalene,
1-[N-(2-hydroxyethyl)-N-methylaminomethyl]-4,6-dimethoxy-1,2,3,4-tetrahydronaphthalene,
1-[N-(2-hydroxyethyl)-N-methylaminomethyl]-4,5,6-trichloro-1,2,3,4-tetrahydronaphthalene,
1-[N-(2-hydroxyethyl)-N-methylaminomethyl]-1,2-benzo-6-chloro-cycloheptane, and
1-[N-(2-hydroxyethyl)-N-methylaminomethyl]-1,2-benzo-8-chloro-cycloheptane, and
1-[N-(2-hydroxyethyl)-N-methylaminomethyl]-1,2-benzo-cycloheptane;
there are obtained the following respective compounds:
2-methyl-5-methoxy-1,3,4,8,9,9a-hexahydro-2H-indeno[1,7-cd]azepine (HBr salt, mp 250°–252° C.),
2-methyl-1,3,4,8,9,9a-hexahydro-2H-indeno[1,7-cd]azepine (HBr salt, mp 262°–263° C.),
2-methyl-5-nitro-1,3,4,8,9,9a-hexahydro-2H-indeno[1,7-cd]azepine,
2-methyl-5-chloro-1,3,4,8,9,9a-hexahydro-2H-indeno[1,7-cd]azepine (HBr salt, mp 262°–263° C.),
2-methyl-5-methoxy-1,2,3,4,8,9,10,10a-octahydronaphth[1,8-cd]azepine (HCl salt, mp 214°–215° C.),
2-methyl-5-chloro-1,2,3,4,8,9,10,10a-octahydronaphth[1,8-cd]azepine (HCl salt, mp 233°–234° C.),
2-methyl-7-chloro-1,2,3,4,8,9,10,10a-octahydronaphth[1,8-cd]azepine (HCl salt, mp 224°–226° C.),
2-methyl-5,7-dimethoxy-1,2,3,4,8,9,10,10a-octahydronaphth[1,8-cd]azepine,
2-methyl-5,6,7-trichloro-1,2,3,4,8,9,10,10a-octahydronaphth[1,8-cd]azepine,
2-methyl-5-chloro-1,3,4,8,9,10,11,11a-octahydro-2H-cyclohepta[c,d][3]benzazepine (HBr salt, mp 191°–193° C.), 2-methyl-7-chloro-1,3,4,8,9,10,11,11a-octahydro-2H-cyclohepta[c,d][3]benzazepine (HBr salt, mp 209°-211° C.), and 2-methyl-1,3,4,8,9,10,11,11a-octahydro-2H-cyclohepta[c,d][3]benzazepine (HCl salt, mp 184°-186° C.).

EXAMPLE 6

2-Methyl-5-chloro-1,3,4,8,9,9a-hexahydro-2H-indeno[1,7-cd]azepine

6A. Formula I Where R is Methyl, $R^1$ and $R^2$ are Hydrogen, $R^3$ is Chloro, and Y is —$(CH_2)_2$—

A solution of 600 mg (2.5 mmol) of 2-methyl-3-oxo-5-chloro-1,3,4,8,9,9a-hexahydro-2H-indeno[1,7-cd]azepine, a compound of Formula 16 prepared, for example, as described in Preparation 16, dissolved in 25 ml of THF was combined with 8 ml of a 1M solution of $BF_3$.THF in tetrahydrofuran. The reaction mixture was stored at ambient temperature for 16 hours. A few ml of methanol was added dropwise and the solvents were removed under vacuum. The residue was treated with 25 ml of 5% HCl and digested on a steam bath for 3 hours. After cooling to ambient temperature, the aqueous solution was washed once with ether, made alkaline with NaOH, and extracted with ether. The ether extract was concentrated to give 2-methyl-5-chloro-1,3,4,8,9,9a-hexahydro-2H-indeno[1,7-cd]azepine, a compound of Formula I, as the free base; (HBr salt, ethanol, mp 279°-281° C.).

6B. Formula I Where R is Methyl, Varying $R^1$, $R^2$, $R^3$, and Y

By following the procedure of part A and substituting for 2-methyl-3-oxo-5-chloro-1,3,4,8,9,9a-hexahydro-2H-indeno[1,7-cd]azepine the following:

2-methyl-3-oxo-5-methoxy-1,3,4,8,9,9a-hexahydro-2H-indeno[1,7-cd]azepine, 2-methyl-3-oxo-1,3,4,8,9,9a-hexahydro-2H-indeno[1,7-cd]azepine, 2-methyl-3-oxo-5-nitro-1,3,4,8,9,9a-hexahydro-2H-indeno[1,7-cd]azepine, 2-methyl-3-oxo-5-methoxy-1,2,3,4,8,9,10,10a-octahydronaphth[1,8-cd]azepine, 2-methyl-3-oxo-1,2,3,4,8,9,10,10a-octahydronaphth[1,8-cd]azepine, 2-methyl-3-oxo-5-chloro-1,2,3,4,8,9,10,10a-octahydronaphth[1,8-cd]azepine, 2-methyl-3-oxo-7-chloro-1,2,3,4,8,9,10,10a-octahydronaphth[1,8-cd]azepine, 2-methyl-3-oxo-5,7-dimethoxy-1,2,3,4,8,9,10,10a-octahydronaphth[1,8-cd]azepine, 2-methyl-3-oxo-5,6,7-trichloro-1,2,3,4,8,9,10,10a-octahydronaphth[1,8-cd]azepine, 2-methyl-3-oxo-5-chloro-1,3,4,8,9,10,11,11a-octahydro-2H-cyclohepta[c,d][3]benzazepine, 2-methyl-3-oxo-7-chloro-1,3,4,8,9,10,11,11a-octahydro-2H-cyclohepta[c,d][3]benzazepine, and 2-methyl-3-oxo-1,3,4,8,9,10,11,11a-octahydro-2H-cyclohepta[c,d][3]benzazepine;

there are obtained the following respective compounds:

2-methyl-5-methoxy-1,3,4,8,9,9a-hexahydro-2H-indeno[1,7-cd]azepine (HBr salt, mp 250°-252° C.), 2-methyl-1,3,4,8,9,9a-hexahydro-2H-indeno[1,7-cd]azepine (HBr salt, mp 262°-263° C.), 2-methyl-5-nitro-1,3,4,8,9,9a-hexahydro-2H-indeno[1,7-cd]azepine, 2-methyl-5-methoxy-1,2,3,4,8,9,10,10a-octahydronaphth[1,8-cd]azepine (HCl salt, mp 214°-215° C.), 2-methyl-1,2,3,4,8,9,10,10a-octahydronaphth[1,8-cd]azepine (HCl salt, mp 185°-186° C.), 2-methyl-5-chloro-1,2,3,4,8,9,10,10a-octahydronaphth[1,8-cd]azepine (HCl salt, mp 233°-234° C.), 2-methyl-7-chloro-1,2,3,4,8,9,10,10a-octahydronaphth[1,8-cd]azepine (HCl salt, mp 224°-226° C.), 2-methyl-5,7-dimethoxy-1,2,3,4,8,9,10,10a-octahydronaphth[1,8-cd]azepine, 2-methyl-5,6,7-trichloro-1,2,3,4,8,9,10,10a-octahydronaphth[1,8-cd]azepine, 2-methyl-5-chloro-1,3,4,8,9,10,11,11a-octahydro-2H-cyclohepta[c,d][3]benzazepine (HBr salt, mp 191°-193° C.), 2-methyl-7-chloro-1,3,4,8,9,10,11,11a-octahydro-2H-cyclohepta[c,d][3]benzazepine (HBr salt, mp 209°-211° C.), and 2-methyl-1,3,4,8,9,10,11,11a-octahydro-2H-cyclohepta[c,d][3]benzazepine (HCl salt, mp 184°-186° C.).

EXAMPLE 7

2-Methyl-5-hydroxy-1,2,3,4,8,9,10,10a-octahydronaphth[1,8-cd]azepine

7A. Formula I Where R is Methyl, $R^1$ and $R^2$ are Hydrogen, $R^3$ is Hydroxy, and Y is —$(CH_2)_3$—

A solution of 2.31 g (10 mmol) of 2-methyl-5-methoxy-1,2,3,4,8,9,10,10a-octahydronaphth[1,8-cd]azepine in 25 ml of dichloromethane was cooled to −70° C., and 20 ml of 1M boron tribromide in dichloromethane was added. The mixture was allowed to warm to room temperature and then cooled to −40° C., and then treated with 10 ml of methanol. Solvents were removed under reduced pressure and the residue was crystallized from methanol ether to afford 1.8 g (60%) of 2-methyl-5-hydroxy-1,2,3,4,8,9,10,10a-octahydronaphth[1,8-cd]azepine (HBr salt, mp 217°-218° C.).

7B. Formula I Where $R^1$, $R^2$ and/or $R^3$ are Hydroxy

Similarly, by following the procedure of part A above and substituting for 2-methyl-5-methoxy-1,2,3,4,8,9,10,10a-octahydronaphth[1,8-cd]azepine the other compounds of Formula I where $R^1$, $R^2$ and/or $R^3$ are methoxy, there are obtained the corresponding hydroxy compounds of Formula I.

EXAMPLE 8

2-Methyl-5-chloro-1,2,3,4,8,9,10,10a-octahydronaphth[1,8-cd]azepine hydrochloride 8A. Hydrochloride Salt of Formula I Where R is Methyl, $R^1$ and $R^2$ are Hydrogen, $R^3$ is Chloro, and Y is —$(CH_2)_3$—

2-Methyl-5-chloro-1,2,3,4,8,9,10,10a-octahydronaphth[1,8-cd]azepine was dissolved in isopropanol (200 ml) and the solution was added to a solution of hydrogen chloride (10.0 g) in isopropanol (150 ml). The hydrochloride salt was collected by filtration and dried under vacuum (m.p. 233°-234° C.).

8B. Hydrochloride Salts of Formula I

Similarly, by following the procedure of part A above and substituting for 2-methyl-5-chloro-1,2,3,4,8,9,10,10a-octahydronaphth[1,8-cd]azepine the other free bases of Formula I, there are obtained the corresponding hydrochloride salts.

EXAMPLE 9

2-Methyl-5-chloro-1,3,4,8,9,10,11,11a-octahydro-2H-cyclohepta[c,d][3]benzazepine hydrobromide

9A. HBr Salt of Formula I where R is Methyl, $R^1$ and $R^2$ are Hydrogen, $R^3$ is Chloro, and Y is —$(CH_2)_3$—

2-Methyl-5-chloro-1,3,4,8,9,10,11,11a-octahydro-2H-cyclohepta[c,d][3]benzazepine is dissolved in ethyl acetate (50 ml) and the solution is added to a solution of bromic acid (1.25 g) in isopropanol (50 ml). The hydrobromide salt is collected by filtration, washed with ethyl acetate and dried under vacuum at 50° C. (m.p. 191°–193° C.).

9B. Hydrobromide Salts of Formula I

Similarly, by following the procedure of part A above and substituting for 2-methyl-5-chloro-1,3,4,8,9,10,11,11a-octahydro-2H-cyclohepta[c,d][3-]benzazepine the other free bases of Formula I, there are obtained the corresponding hydrobromide salts.

EXAMPLE 10

This example illustrates the preparation of a representative pharmaceutical formulation for oral administration containing an active compound of Formula I, e.g., 2-methyl-5-chloro-1,2,3,4,8,9,10,10a-octahydronaphth[1,8-cd]azepine hydrochloride.

| Ingredients | Quantity per tablet, mgs. |
| --- | --- |
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Examples 1–9, can be used as the active compound in the preparation of the orally administrable formulations of this example.

EXAMPLE 11

This example illustrates the preparation of another representative pharmaceutical formulation for oral administration, containing an active compound of Formula I, e.g., 2-methyl-5-chloro-1,2,3,4,8,9,10,10a-octahydronaphth[1,8-cd]azepine hydrochloride.

| Ingredients | Quantity per tablet, mgs. |
| --- | --- |
| Active compound | 400 |
| cornstarch | 50 |
| lactose | 145 |
| magnesium stearate | 5 |

The above ingredients are mixed intimately and pressed into single scored tablets.

Other compounds of Formula I, such as those prepared in accordance with Examples 1–9, can be used as the active compound in the preparation of the orally administrable formulations of this example.

EXAMPLE 12

This example illustrates the preparation of a representative pharmaceutical formulation containing an active compound of Formula I, e.g., 2-methyl-5-chloro-1,2,3,4,8,9,10,10a-octahydronaphth[1,8-cd]azepine hydrochloride.

An suspension for oral administration is prepared having the following composition:

| Ingredients | |
| --- | --- |
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Other compounds of Formula I, such as those prepared in accordance with Examples 1–9, can be used as the active compound in the preparation of the orally administrable formulations of this example.

EXAMPLE 13

This example illustrates the preparation of a representative pharmaceutical formulation containing an active compound of Formula I, e.g., 2-methyl-5-chloro-1,2,3,4,8,9,10,10a-octahydronaphth[1,8-cd]azepine hydrochloride.

An injectable preparation buffered to a pH of 7 is prepared having the following composition:

| Ingredients | |
| --- | --- |
| Active compound | 0.2 g |
| Sodium Acetate Buffer Solution (0.4 M) | 2.0 ml |
| HCl (1N) | q.s. to pH 7 |
| water (distilled, sterile) | q.s. to 20 ml |

Other compounds of Formula I, such as those prepared in accordance with Examples 1–9, can be used as the active compound in the preparation of the injectable formulations of this example.

EXAMPLE 14

This example illustrates the preparation of a representative pharmaceutical formulation for topical application containing an active compound of Formula I, e.g., 2-methyl-5-chloro-1,2,3,4,8,9,10,10a-octahydronaphth[1,8-cd]azepine hydrochloride.

| Ingredients | grams |
| --- | --- |
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula I, such as those prepared in accordance with Examples 1–9, can be used as the active compound in the preparation of the topical formulations of this example.

EXAMPLE 15

This example illustrates the preparation of a representative pharmaceutical formulation containing an active compound of Formula I, e.g., 2-methyl-5-chloro-1,2,3,4,8,9,10,10a-octahydronaphth[1,8-cd]azepine hydrochloride.

A suppository totalling 2.5 grams is prepared having the following composition:

| Active compound | 500 mg |
| --- | --- |
| witespol H-15* | balance |

(*triglycerides of saturated vegetable fatty acid; a product of Riches-Nelson, Inc., New York, N.Y.).

Other compounds of Formula I, such as those prepared in accordance with Examples 1-9, can be used as the active compound in the preparation of the suppository formulations of this example.

EXAMPLE 16

Determination of Activity Utilizing 5-$HT_{1A}$ Binding Affinity Assay

This procedure is a modification of a procedure initially described by Gozlan, et al., Nature, 305 140-142 (1983).

Male Sprague-Dawley rats are killed by a blow to the head and the brains rapidly removed and dissected. Cerebral cortex and hippocampal tissues (areas rich in $5HT_{1A}$ sites) are homogenised separately in 25 ml ice cold Tris buffer (50 mM Tris HCl pH 7.7 at 25° C.) and centrifuged at 38,000 gav for 10 min. After the third wash the resuspended pellet is incubated at 37° C. for 10 minutes. Membranes are then collected by centrifugation as above and the final pellet is resuspended in 50 mM Tris HCl, 5 mM $MgSO_4$, 0.5 mM EDTA buffer (pH 7.4 at 37° C.).

Aliquots of the final membrane suspension (0.8-1.0 mg protein) are incubated for 10 min at 37° C. with [$^3$H]-8-OH-DPAT (8-hydroxy-2-[di-n-propylamino]tetralin) (1.5 nM) in the presence or absence of 13 concentrations of the competing drug in a final volume of 2 ml Tris assay buffer (50 mM Tris HCl, pH 7.4). Non-specific binding is determined using 10 mcM 5HT or 3 mcM buspirone. Bound radioactivity is separated from free by vacuum filtration over Whatman GF/B filters with 3×5 ml washes of ice cold buffer and determined by liquid scintillation spectrophotometry.

The recognition site labelled by [$^3$H]-8-OH-DPAT on rat membranes is characteristic of the $5HT_{1A}$ site as shown by the high affinity of 5HT and $5HT_{1A}$ selective compounds, 8-OH-DPAT, Buspirone and WB4101 as compared to the $5HT_2$ selective compound Ketanserin and the $5HT_{1C}/5HT_2$ selective compound Mesulergine.

The compounds of the present invention show activity when tested by this method.

EXAMPLE 17

Determination of Activity Utilizing 5-$HT_{1A}$ Binding Affinity Assay

This procedure is a modification of a procedure initially described by Norman, et al., Mol. Pharmacol., 28 487 (1986).

Male Sprague-Dawley rats are killed by a blow to the head and the brains rapidly removed and dissected. Cerebral cortex and hippocampal tissues (areas rich in $5HT_{1A}$ sites) are homogenised separately in 25 ml ice cold Tris buffer (50 mM Tris HCl pH 7.7 at 25° C.) and centrifuged at 38,000 gav for 10 min. After the third wash the resuspended pellet is incubated at 37° C. for 10 minutes. Membranes were then collected by centrifugation as above and the final pellet was resuspended in 50 mM Tris HCl, 5 mM $MgSO_4$, 0.5 mM EDTA buffer (pH 7.4 at 37° C.).

Washed rat membranes (0.5-1 mg protein) are incubated with [$^3$H]WB4101 (2-[2,6-dimethyoxyphenoxyethyl]amino-methyl-1,4-benzodioxane) (3 nM) for 40 min at 37° C., in the presence or absence of 13 concentrations of the competing drug in a final volume of 2.5 ml Tris assay buffer (50 mM Tris HCl, pH 7.4 at 37° C.). Non-specific binding is determined using 10M 5HT or 3M buspirone. [$^3$H]-WB4101 assays are performed in the presence of a 30 nM prazosin to mask $alpha_1$ adrenoceptors. Bound radioactivity is separated and determined as described in Example 15, above.

The compounds of the present invention show activity when tested by this method.

EXAMPLE 18

Determination of $\alpha_2$ Activity Utilizing The $\alpha_2$ Binding Affinity Assay This procedure is a modification of a procedure initially described by Cheung, et al., Europ. J. Pharmacol., 84 79-85 (1982).

Rat cerebral cortices are homogenised in 20 volumes of Tris buffer (50 mM Tris HCl, 5 mM EDTA: pH 7.4 at 25° C.) using a Polytron PT 10 tissue disruptor. The homogenate is then centrifuged at 38,000 gav for 15 min. The pellet obtained is washed 3 times by resuspension and centrifugation in assay buffer (50 mM Tris HCl, 1 0.5 mM EDTA, pH 7.4 at 25° C.). The final pellet is resuspended in assay buffer for direct use in binding studies.

Washed rat cerebrocortical membranes (1.0 mg.ml$^{-1}$ membrane protein) are incubated for 30 min at 25° C. with [$^3$H]-yohimbine (2.0 nmol. liter$^{-1}$) in the presence or absence of a range of 13 concentrations of the competing ligands in a total volume of 0.25 ml Tris assay buffer. Non-specific binding is defined as the concentration of bound ligand in the presence of $1 \times 10^{-5}$.liter$^{-1}$ phentolamine. Bound radioactivity is separated from free and determined as described above. Following equilibrium (30 min), bound ligand is separated from free by vacuum filtration over Whatman GF/B glass fibre filters. Radioactivity bound to the glass fibre filters is determined by liquid scintillation spectrophotometry.

The compounds of the present invention show activity when tested by this method.

EXAMPLE 19

Determination of Activity Utilizing The Reversal of 8-OH DPAT Effects In Rodents Method The selective ligand from $5HT_{1A}$ receptors, 8-OH-DPAT, induces a distinctive behavioral syndrome in rats. This is measured by the method of Tricklebank, et al. (Europ. J. Pharmacol., 106, 271-282, 1984). Buspirone and compounds of the present invention (3-10 mg.kg$^{-1}$, s.c.). Reduced components of the behavioural syndrome (i.e., forepaw treading, flat body posture), which is indicative of an effect at $5HT_{1A}$ receptors in vivo.

The compounds of the present invention show activity when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound represented by the formula:

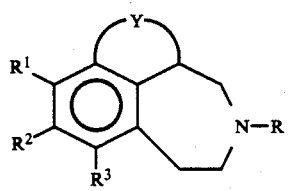

wherein:

R is selected from the group consisting of hydrogen, cyano, lower alkyl, lower alkenyl, and aralkyl;

each of $R^1$, $R^2$ and $R^3$ is independently selected from the group consisting of: hydrogen, hydroxy, halo, trifluoromethyl, nitro, lower alkoxy, lower alkyl, and lower alkylthio; and Y is lower alkylene having from two to four carbon atoms;

or a pharmaceutically acceptable salt thereof.

2. The compound of claim 1 wherein Y is —(CH$_2$)$_2$— or —(CH$_2$)$_3$—.

3. The compound of claim 2 wherein Y is —(CH$_2$)$_2$—.

4. The compound of claim 3 wherein R is alkyl.

5. The compound of claim 4 wherein R is methyl.

6. The compound of claim 5 wherein $R^1$ and $R^2$ are hydrogen, and $R^3$ is not hydrogen.

7. The compound of claim 6 wherein $R^3$ is halo or lower alkoxy.

8. The compound of claim 7 wherein $R^3$ is chloro.

9. The compound of claim 7 wherein $R^3$ is methoxy.

10. The compound of claim 2 wherein Y is —(CH$_2$)$_3$—.

11. The compound of claim 10 wherein R is alkyl.

12. The compound of claim 11 wherein R is methyl.

13. The compound of claim 12 wherein $R^1$ and $R^2$ are hydrogen, and $R^3$ is not hydrogen.

14. The compound of claim 13 wherein $R^3$ is halo or lower alkoxy.

15. The compound of claim 14 wherein $R^3$ is chloro.

16. The compound of claim 14 wherein $R^3$ is methoxy.

17. The compound of claim 1 wherein R is alkyl.

18. The compound of claim 17 wherein R is methyl.

19. The compound of claim 1 wherein $R^1$ and $R^2$ are hydrogen, and $R^3$ is not hydrogen.

20. The compound of claim 19 wherein $R^3$ is halo or lower alkoxy.

21. The compound of claim 20 wherein $R^3$ is chloro.

22. The compound of claim 20 wherein $R^3$ is methoxy.

23. The HCl or HBr salt of a compound of claim 1.

24. A pharmaceutical composition comprising a pharmaceutically acceptable non-toxic excipient and a therapeutically effective amount of a compound of claim 1.

25. A pharmaceutical composition for oral administration comprising a pharmaceutically acceptable non-toxic excipient and a therapeutically effective amount of a compound of claim 1.

26. A method of treating depression, anxiety or hypertension in mammals, which comprises administering to a mammal suffering therewith a therapeutically effective amount of a compound represented by the formula:

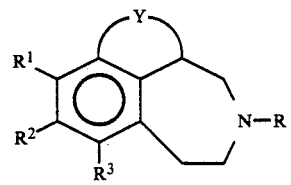

wherein:

R is selected from the group consisting of hydrogen, cyano, lower alkyl, lower alkenyl, and aralkyl;

each of $R^1$, $R^2$ and $R^3$ is independently selected from the group consisting of: hydrogen, hydroxy, halo, trifluoromethyl, nitro, lower alkoxy, lower alkyl, and lower alkylthio; and Y is lower alkylene having from two to four carbon atoms; or a pharmaceutically acceptable salt thereof.

27. The method of claim 26 which comprises administering to a mammal suffering with depression a therapeutically effective amount of said compound.

28. The method of claim 26 which comprises administering to a mammal suffering with anxiety a therapeutically effective amount of said compound.

29. The method of claim 26 which comprises administering to a mammal suffering with hypertension a therapeutically effective amount of said compound.

* * * * *